(12) United States Patent
Serdy et al.

(10) Patent No.: US 7,815,826 B2
(45) Date of Patent: Oct. 19, 2010

(54) MANUFACTURING PROCESS, SUCH AS THREE-DIMENSIONAL PRINTING, INCLUDING SOLVENT VAPOR FILMING AND THE LIKE

(75) Inventors: James G. Serdy, Boston, MA (US); Emanuel M. Sachs, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 734 days.

(21) Appl. No.: 11/579,783

(22) PCT Filed: May 12, 2005

(86) PCT No.: PCT/US2005/016698

§ 371 (c)(1),
(2), (4) Date: Nov. 7, 2006

(87) PCT Pub. No.: WO2005/114322

PCT Pub. Date: Dec. 1, 2005

(65) Prior Publication Data

US 2008/0032083 A1 Feb. 7, 2008

Related U.S. Application Data

(60) Provisional application No. 60/570,412, filed on May 12, 2004.

(51) Int. Cl.
*B29C 67/20* (2006.01)

(52) U.S. Cl. .................... 264/49; 264/83; 264/122; 264/308; 264/344

(58) Field of Classification Search ........... None
See application file for complete search history.

(56) References Cited

U.S. PATENT DOCUMENTS 3,566,871 A 3/1971 Richter (Continued)

FOREIGN PATENT DOCUMENTS

JP 6298639 10/1994

(Continued)

OTHER PUBLICATIONS

Tsang, Valerie Liu; Bhatia, Sangeeta N.; Three dimensional tissue fabrication; Advanced Drug Delivery Reviews; 2004; pp. 1635-1647; vol. 56; Elsevier; http://lmrt.mit.edu/publications/liu2004.pdf; USA.

(Continued)

*Primary Examiner*—Mary Lynn F Theisen
(74) *Attorney, Agent, or Firm*—Steven J. Weissburg

(57) ABSTRACT

Methods of manufacturing an article use three-dimensional printing for a portion of the manufacturing. Three-dimensionally printing is conducted onto a powder bed which contains both organic-solvent-soluble, water-insoluble particles and water soluble, organic-solvent-insoluble particles. The water-soluble particles which may be selected for properties such as size and may include more than one substance. The organic-solvent-insoluble particles may further include at least one substantially insoluble substance such as a member of the calcium phosphate family. Printing may be done using an aqueous binder liquid. After removal of unbound powder, the preform may be exposed to the vapor of an organic solvent which causes the particles of organic-soluble-polymer to fuse to each other. This may further be followed by dissolving out the water-soluble particles, if such particles were present in the powder. Solvent vapor fusing together with the use of porogen particles may also be used in manufacturing methods other than 3DP. Rather than using organic solvent, heat responsive particles can be used, and can be filmed by elevated temperatures. Articles that may be produced by the described methods exhibit features such as a high porosity and an ability to undergo large deformations without breaking, and by at least partial springback from such deformation. The springback may be substantially instantaneous or may be time-dependent involving a time period of at least several seconds.

49 Claims, 24 Drawing Sheets

U.S. PATENT DOCUMENTS

| | | |
|---|---|---|
| 4,045,418 A | 8/1977 | Sinclair |
| 4,057,537 A | 11/1977 | Sinclair |
| 4,157,437 A | 6/1979 | Okuzumi et al. |
| 4,186,448 A | 2/1980 | Brekke |
| 4,243,775 A | 1/1981 | Rosensaft et al. |
| 4,379,138 A | 4/1983 | Pitt et al. |
| 4,547,327 A | 10/1985 | Bruins et al. |
| 4,595,713 A | 6/1986 | St. John |
| 4,605,730 A | 8/1986 | Shalaby et al. |
| 4,636,526 A | 1/1987 | Dorman et al. |
| 4,637,931 A | 1/1987 | Schmitz |
| 4,643,734 A | 2/1987 | Lin |
| 4,650,488 A | 3/1987 | Bays et al. |
| 4,673,355 A | 6/1987 | Farris et al. |
| 4,700,704 A | 10/1987 | Jamiolkowski et al. |
| 4,719,246 A | 1/1988 | Murdoch et al. |
| 4,728,570 A | 3/1988 | Ashman et al. |
| 4,728,721 A | 3/1988 | Yamamoto et al. |
| 4,780,450 A | 10/1988 | Sauk et al. |
| 4,800,219 A | 1/1989 | Murdoch et al. |
| 4,843,112 A | 6/1989 | Gerhart et al. |
| 4,869,906 A | 9/1989 | Dingeldein et al. |
| 4,994,074 A | 2/1991 | Bezwada et al. |
| 5,017,518 A | 5/1991 | Hirayama et al. |
| 5,034,422 A | 7/1991 | Triolo et al. |
| 5,133,739 A | 7/1992 | Bezwada et al. |
| 5,171,834 A | 12/1992 | Funaki |
| 5,204,055 A | 4/1993 | Sachs et al. |
| 5,250,584 A | 10/1993 | Ikada et al. |
| 5,294,393 A | 3/1994 | Toki et al. |
| 5,322,925 A | 6/1994 | Muth et al. |
| 5,333,042 A | 7/1994 | Brennan et al. |
| 5,336,700 A | 8/1994 | Murray |
| 5,338,772 A | 8/1994 | Bauer et al. |
| 5,340,656 A | 8/1994 | Sachs et al. |
| 5,348,788 A | 9/1994 | White |
| 5,356,629 A | 10/1994 | Sander et al. |
| 5,366,756 A | 11/1994 | Chesterfield et al. |
| 5,387,380 A | 2/1995 | Cima et al. |
| 5,403,347 A | 4/1995 | Roby et al. |
| 5,433,751 A | 7/1995 | Christel et al. |
| 5,442,033 A | 8/1995 | Bezwada |
| 5,443,483 A | 8/1995 | Kirsch |
| 5,466,262 A | 11/1995 | Saffran |
| 5,475,063 A | 12/1995 | Kaplan et al. |
| 5,490,962 A | 2/1996 | Cima et al. |
| 5,492,697 A | 2/1996 | Boyan et al. |
| 5,496,371 A | 3/1996 | Eppley et al. |
| 5,514,378 A | 5/1996 | Mikos et al. |
| 5,518,680 A | 5/1996 | Cima et al. |
| 5,522,895 A | 6/1996 | Mikos |
| 5,531,794 A | 7/1996 | Takagi et al. |
| 5,552,454 A | 9/1996 | Kretschmann et al. |
| 5,578,086 A | 11/1996 | Prescott |
| 5,593,425 A | 1/1997 | Bonutti et al. |
| 5,607,474 A | 3/1997 | Athanasiou et al. |
| 5,610,266 A | 3/1997 | Buchholz |
| 5,626,861 A | 5/1997 | Laurencin et al. |
| 5,639,402 A | 6/1997 | Barlow et al. |
| 5,674,290 A | 10/1997 | Li |
| 5,676,699 A | 10/1997 | Gogolewski et al. |
| 5,677,355 A | 10/1997 | Shalaby et al. |
| 5,686,091 A | 11/1997 | Leong et al. |
| 5,697,976 A | 12/1997 | Chesterfield et al. |
| 5,711,960 A | 1/1998 | Shikinami |
| 5,716,413 A | 2/1998 | Walter et al. |
| 5,735,875 A | 4/1998 | Bonutti et al. |
| 5,747,637 A | 5/1998 | Shinoda et al. |
| 5,766,618 A | 6/1998 | Laurencin et al. |
| 5,769,899 A | 6/1998 | Schwartz et al. |
| 5,769,935 A | 6/1998 | Swan |
| 5,776,193 A | 7/1998 | Kwan et al. |
| 5,800,542 A | 9/1998 | Li |
| 5,824,088 A | 10/1998 | Kirsch |
| 5,830,493 A | 11/1998 | Yokota et al. |
| 5,834,150 A | 11/1998 | Brennan et al. |
| 5,863,297 A | 1/1999 | Walter et al. |
| 5,866,155 A | 2/1999 | Laurencin et al. |
| 5,869,170 A | 2/1999 | Cima et al. |
| 5,876,446 A | 3/1999 | Agrawal et al. |
| 5,876,452 A | 3/1999 | Athanasiou et al. |
| 5,919,234 A | 7/1999 | Lemperle et al. |
| 5,934,343 A | 8/1999 | Gaylo et al. |
| 5,947,893 A | 9/1999 | Agrawal et al. |
| 5,958,314 A | 9/1999 | Draenert |
| 5,977,204 A | 11/1999 | Boyan et al. |
| 5,997,568 A | 12/1999 | Liu |
| 6,013,853 A | 1/2000 | Athanasiou et al. |
| 6,077,989 A | 6/2000 | Kandel et al. |
| 6,110,484 A | 8/2000 | Sierra |
| 6,139,574 A | 10/2000 | Vacanti et al. |
| 6,146,892 A | 11/2000 | Ma et al. |
| 6,147,135 A | 11/2000 | Yuan et al. |
| 6,165,486 A | 12/2000 | Marra et al. |
| 6,176,874 B1 | 1/2001 | Vacanti et al. |
| 6,183,515 B1 | 2/2001 | Barlow et al. |
| 6,187,047 B1 | 2/2001 | Kwan et al. |
| 6,203,573 B1 | 3/2001 | Walter et al. |
| 6,203,574 B1 | 3/2001 | Kawamura |
| 6,206,924 B1 | 3/2001 | Timm |
| 6,213,168 B1 | 4/2001 | Gaylo et al. |
| 6,228,117 B1 | 5/2001 | De Bruijn et al. |
| 6,228,954 B1 | 5/2001 | Kaplan et al. |
| 6,241,771 B1 | 6/2001 | Gresser et al. |
| 6,277,394 B1 | 8/2001 | Sierra |
| 6,277,927 B1 | 8/2001 | Roby et al. |
| 6,281,257 B1 | 8/2001 | Ma et al. |
| 6,283,997 B1 | 9/2001 | Garg et al. |
| 6,294,187 B1 | 9/2001 | Boyce et al. |
| 6,296,667 B1 | 10/2001 | Johnson et al. |
| 6,303,697 B1 | 10/2001 | Yuan et al. |
| 6,306,424 B1 | 10/2001 | Vyakarnam et al. |
| 6,316,091 B1 | 11/2001 | Richart et al. |
| 6,333,029 B1 | 12/2001 | Vyakarnam et al. |
| 6,336,480 B2 | 1/2002 | Gaylo et al. |
| 6,342,065 B1 | 1/2002 | Shalaby |
| 6,344,496 B1 | 2/2002 | Niederauer et al. |
| 6,361,789 B1 | 3/2002 | Zuccato et al. |
| 6,376,573 B1 | 4/2002 | White et al. |
| 6,406,498 B1 | 6/2002 | Tormala et al. |
| 6,441,073 B1 | 8/2002 | Tanaka et al. |
| 6,454,811 B1 | 9/2002 | Sherwood et al. |
| 6,458,162 B1 | 10/2002 | Koblish et al. |
| 6,471,993 B1 | 10/2002 | Shastri et al. |
| 6,494,898 B1 | 12/2002 | Roby et al. |
| 6,506,213 B1 | 1/2003 | Mandel et al. |
| 6,514,286 B1 | 2/2003 | Leatherbury et al. |
| 6,518,323 B1 | 2/2003 | Scheying et al. |
| 6,520,997 B1 | 2/2003 | Pekkarinen et al. |
| 6,530,958 B1 | 3/2003 | Cima et al. |
| 6,534,084 B1 | 3/2003 | Vyakarnam et al. |
| 6,540,784 B2 | 4/2003 | Barlow et al. |
| 6,548,002 B2 | 4/2003 | Gresser et al. |
| 6,632,446 B1 | 10/2003 | Hubbell et al. |
| 6,656,489 B1 | 12/2003 | Mahmood et al. |
| 6,673,285 B2 | 1/2004 | Ma |
| 6,692,761 B2 | 2/2004 | Mahmood et al. |
| 6,712,850 B2 | 3/2004 | Vyakarnam et al. |
| 6,712,851 B1 | 3/2004 | Lemperle et al. |
| 6,719,795 B1 | 4/2004 | Cornwall et al. |
| 6,737,073 B2 | 5/2004 | Mahmood et al. |
| 6,747,121 B2 | 6/2004 | Gogolewski |
| 6,764,517 B2 | 7/2004 | Yamamoto et al. |
| 6,770,717 B2 | 8/2004 | Kim et al. |

| | | |
|---|---|---|
| 6,821,916 B2 | 11/2004 | Myoi et al. |
| 6,863,899 B2 | 3/2005 | Koblish et al. |
| 6,867,240 B2 | 3/2005 | Ma |
| 6,872,387 B1 | 3/2005 | Ma |
| 6,913,765 B2 | 7/2005 | Li et al. |
| 6,932,610 B2 | 8/2005 | Ono et al. |
| 6,946,143 B2 | 9/2005 | Kim et al. |
| 6,949,251 B2 | 9/2005 | Dalal et al. |
| 6,982,058 B2 | 1/2006 | Jacobson |
| 6,998,134 B2 | 2/2006 | Schmidmaier et al. |
| 7,004,977 B2 | 2/2006 | Ashman |
| 7,019,106 B2 | 3/2006 | Yamamoto et al. |
| 7,022,522 B2 | 4/2006 | Guan et al. |
| 7,045,125 B2 | 5/2006 | Erbe et al. |
| 7,049,348 B2 | 5/2006 | Evans et al. |
| 7,063,726 B2 | 6/2006 | Crouch et al. |
| 7,077,866 B2 | 7/2006 | Gresser et al. |
| 7,087,200 B2 | 8/2006 | Taboas et al. |
| 7,128,753 B1 | 10/2006 | Bonutti et al. |
| 7,135,025 B2 | 11/2006 | Pohjonen et al. |
| 7,153,519 B2 | 12/2006 | Hubbell et al. |
| 7,160,492 B2 | 1/2007 | King |
| 7,166,133 B2 | 1/2007 | Evans et al. |
| 7,174,282 B2 | 2/2007 | Hollister et al. |
| 7,189,263 B2 | 3/2007 | Erbe et al. |
| 7,192,450 B2 | 3/2007 | Brauker et al. |
| 7,208,222 B2 | 4/2007 | Rolfe et al. |
| 7,230,039 B2 | 6/2007 | Trieu et al. |
| 7,250,550 B2 | 7/2007 | Overby et al. |
| 2002/0058718 A1 | 5/2002 | Ma et al. |
| 2002/0182241 A1 | 12/2002 | Borenstein et al. |
| 2003/0006534 A1 | 1/2003 | Taboas et al. |
| 2003/0073158 A1 | 4/2003 | Ma |
| 2003/0074096 A1 | 4/2003 | Das et al. |
| 2003/0114936 A1* | 6/2003 | Sherwood et al. ........ 623/23.58 |
| 2003/0180344 A1 | 9/2003 | Wise et al. |
| 2004/0006125 A1 | 1/2004 | Remington et al. |
| 2004/0006146 A1 | 1/2004 | Evans et al. |
| 2004/0026811 A1 | 2/2004 | Murphy et al. |
| 2005/0042253 A1 | 2/2005 | Farrar et al. |
| 2005/0169893 A1 | 8/2005 | Koblish et al. |
| 2005/0208271 A1* | 9/2005 | Fasching et al. ............ 428/156 |
| 2005/0214340 A1 | 9/2005 | Erbe et al. |
| 2005/0246021 A1 | 11/2005 | Ringeisen et al. |
| 2006/0008504 A1 | 1/2006 | Kerr et al. |
| 2006/0115644 A1 | 6/2006 | Ma et al. |
| 2006/0121084 A1 | 6/2006 | Borden et al. |
| 2006/0210598 A1 | 9/2006 | Evans et al. |
| 2006/0246121 A1 | 11/2006 | Ma et al. |
| 2006/0280775 A1 | 12/2006 | Ashammakhi et al. |
| 2007/0036844 A1 | 2/2007 | Ma et al. |
| 2007/0093912 A1 | 4/2007 | Borden |
| 2007/0116739 A1 | 5/2007 | Calhoun et al. |
| 2007/0129810 A1 | 6/2007 | Farrar et al. |

FOREIGN PATENT DOCUMENTS

| | | |
|---|---|---|
| WO | 9200401 | 1/1992 |
| WO | 9215440 | 3/1992 |
| WO | 0229966 | 4/2002 |
| WO | 03000480 | 1/2003 |
| WO | 03024316 | 3/2003 |
| WO | 03057844 | 7/2003 |

OTHER PUBLICATIONS

Lee, Spp-Hong; Kim, Byung-Soo; Soo, Hyum Kim; Sun, Woong Kang; Young, Ha Kim; Thermally produced biodegradable scaffolds for cartilage tissue engineering : Special topic on tissue engineering; Macromolecular Bioscience; 2004; vol. 4; Wiley-VCH; http://www3.interscience.wiley.com/cgi-bin/abstract/109585571/AB-STRACT8; Germany.

Antonov, E.N. ; Bagratashvili, V. N. ; Whitaker, M.J. ; Barry, J.J. A. ; Shakesheff, K.M. ; Konovalov, A.N. ; Popov, V.K. ; Howdle, S.M. ; Three-Dimensional Bioactive and Biodegradable Scaffolds Fabricated by Surface-Selective Laser Sintering; 2004; vol. 17; Wiley-VCH; Weinheim; http://www3.interscience.wiley.com/cgi-bin/abstract/109859148/ABSTRACT; Germany.

Murphy, William L.; Dennis, Robert G.; Kileny, Joel L.; Mooney, David J.; Salt Fusion: An Approach to Improve Pore Interconnectivity within Tissue Engineering Scaffolds; 2002; vol. 8; Mary Ann Liebert, Inc.; http://www.liebertonline.com/doi/abs/10.1089/107632702753503045; USA.

Liao, Chin Chen, Jui Chen, Chiang, Lin and Chang; Fabrication of Porous Biodegradable Polymer Scaffolds Using a solvent Merging/Particulate Leaching Method; Porous Biodegradable Polymer Scaffolds; 2001; pp. 676-681; John Wiley & Sons, Inc.; USA.

International Search Report, PCT/US2005/016698, mailed on Jan. 29, 2007.

Written Opinion, PCT/US2005/016698, mailed on Jan. 29, 2007.

Harris et al, Open pore biodegradable matrices formed with gas foaming, J. Biomed Mater Res, 1998, 42, 396-402.

Office action mailed Jan. 6, 2009 in U.S. Appl. No. 11/127,298.

Office action mailed Nov. 10, 2009 in U.S. Appl. No. 11/127,298.

* cited by examiner

Heavily bled                Lightly bled

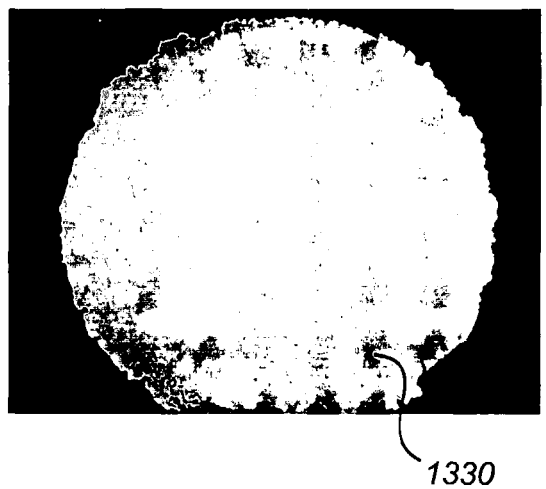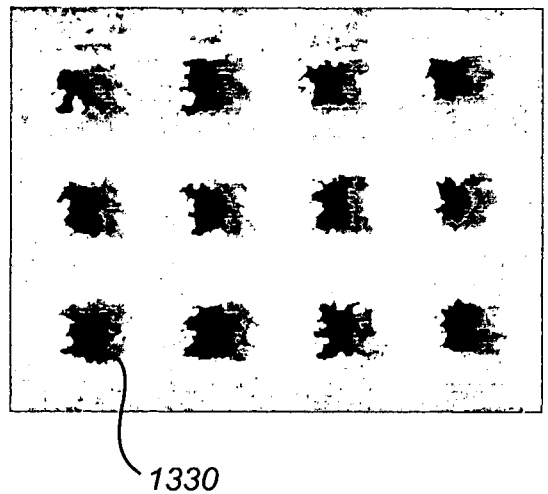
*Fig. 13A*              *Fig. 13B*

20% PCL, 20% TCP, 60% Sugar

MANUFACTURING PROCESS, SUCH AS THREE-DIMENSIONAL PRINTING, INCLUDING SOLVENT VAPOR FILMING AND THE LIKE

RELATED DOCUMENTS

This application claims priority to and benefit of the filing date of U.S. Provisional Patent Application 60/570,412, filed on May 12, 2004, in the names of J. Serdy et al, entitled MANUFACTURING PROCESS, SUCH AS THREE-DIMENSIONAL PRINTING, INCLUDING SOLVENT VAPOR FUSING, which is incorporated fully herein by reference.

BRIEF DESCRIPTION OF THE FIGURES OF THE DRAWING

FIG. 5, in eight subparts are schematic renditions of geometries that can be made according to methods of inventions disclosed herein, with:

FIG. 13A is a digital image of part made by printing an aqueous binder (pure water) into a powder bed composed of polycaprolactone (PCL) 20%, tricalcium phosphate (TCP) 20% and sugar 60%;

FIG. 13B is a digital image of the part shown in FIG. 13A at a higher magnification.

BACKGROUND

Three-dimensional printing (3DP), described in U.S. Pat. No. 5,204,055 (incorporated herein by reference), has proven to be useful in creating structures for a variety of purposes including medical applications such as bone substitutes and tissue scaffolds.

In the basic three-dimensional printing process, a layer of powder has been deposited such as by roller spreading, and then drops of a binder liquid have been dispensed onto the powder layer by techniques related to ink-jet printing. The dispensers have been moved by motion control apparatus and have included raster printing or vector printing, or both, in various combinations. Powder particles have been joined together by the action of the binder liquid. Subsequent powder layers have been sequentially deposited and drops of binder liquid dispensed until the desired three-dimensional object is created. Unbound powder has supported printed regions until the drying of the article and then unbound powder has been removed to leave a printed article or preform.

Binding of the particles has been achieved through any one or more of several mechanisms. One mechanism has been that the binder liquid has sometimes dissolved some of the powder. Then, as the solvent in the binder liquid has evaporated, the material from partially or fully dissolved particles has resolidified so as to form a joined or solid mass of that material. Another mechanism has been that the binder liquid has contained a dissolved binding substance which has been left behind when the volatile part of the binder liquid evaporates, and upon evaporation of the volatile, the dissolved binder substance has solidified around solid particles or solidified such that it is connected to solid particles, thereby binding solid particles together. It has also been possible for both of these effects to occur simultaneously.

Among the materials of interest to be manufactured into articles by 3DP have been polymers. Polymers, especially polymers of medical interest, have tended to require the dispensing of organic solvents from printheads in the 3DP process. A particularly useful solvent has been chloroform, because of the substances which it can dissolve. Organic solvents have tended to be more difficult to dispense from printheads than aqueous solvents, because of their combination of low viscosity and low surface tension. Chloroform in particular, even when it has been successfully dispensed from a printhead, has exhibited further difficulties which relate to how sharp a feature can be created during three-dimensional printing. First of all, chloroform's unusually small surface tension and viscosity have given it extra tendency to spread by capillary action in a powder bed. Additionally, there has been a difficulty associated with the time scale at which chloroform evaporates.

Figure 1:
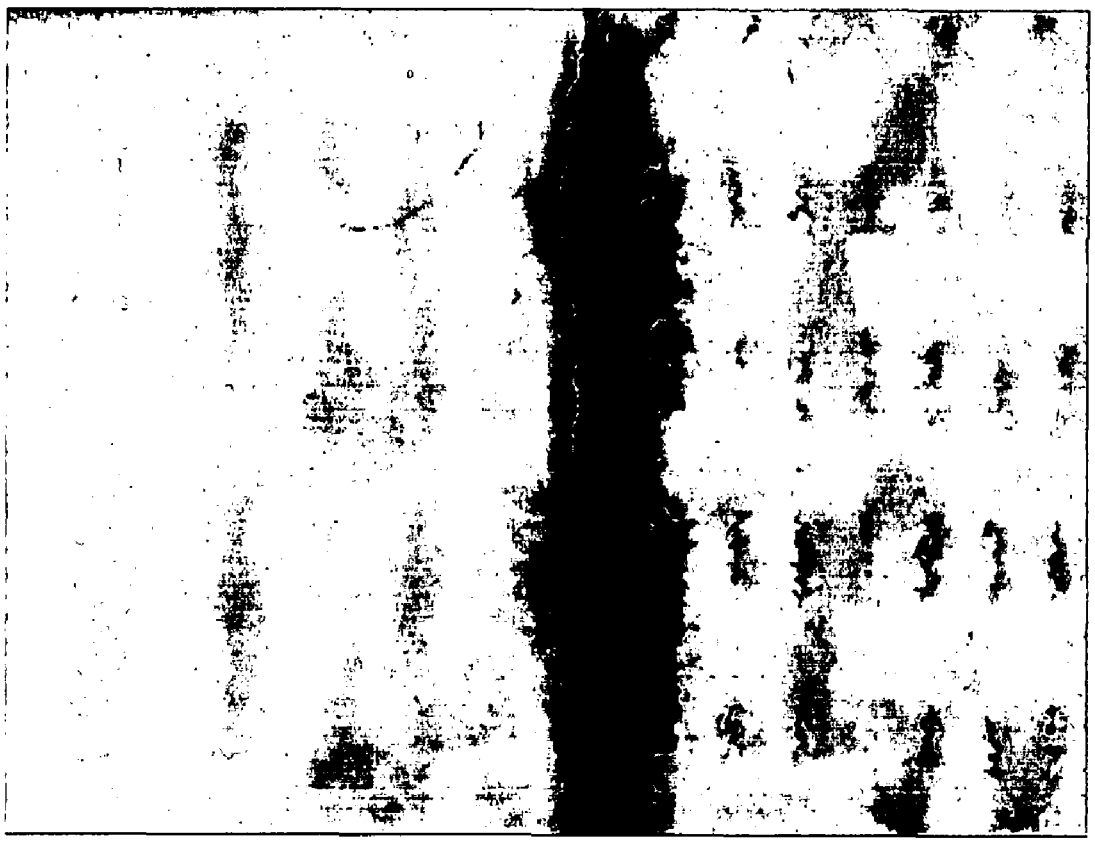
FIG. 1 is a digital image showing a heavily bled three dimensional printing structure on the left and a lightly bled structure on the right.

In three-dimensional printing using dissolution-resolidification, there is a dissolution time scale during which the dissolution of powder particles into the dispensed binder liquid solvent occurs, as governed by the physical properties of the solvent and the solute. (For example, the molecular weight of a polymer can have a strong influence on dissolution time.) There is also an evaporation time scale which describes the evaporation of the dispensed binder liquid, or at least the solvent portion of the dispensed binder liquid, at typical three-dimensional printing conditions such as at room temperature. The evaporation time scale is essentially also the time scale for resolidification to occur. In order for resolidification to be able to occur, there has to be sufficient time for an appropriate amount of dissolution to occur prior to evaporation. If the solvent evaporates before there has been sufficient time for dissolution to occur, little binding can be achieved. With chloroform, the dissolution time scale has been longer than desired, relative to chloroform's evaporation time. Accordingly, in order to achieve sufficient dissolution of powder particles during 3DP, it has been necessary to print chloroform at a relatively high saturation parameter, close to unity. In 3DP, the saturation parameter is a ratio which describes how much of the available inter-particle empty space is actually occupied by binder liquid. A high saturation parameter, especially close to or exceeding unity, has accelerated bleeding (migration) of binder in the powder bed. This in turn has degraded dimensional resolution of printed features and has made it more difficult to remove unbound powder. For example, bleeding has resulted in powder particles being stuck to the printed region which are not really desired to be stuck to the printed region. A comparison of a heavily-bled 3DP structure (left) with a lightly-bled 3DP structure (right) is shown in FIG. 1.

Other difficulties associated with the use of chloroform and similar solvents in 3DP have been the exposure of nearby components of the 3DP machine to the vapor of a solvent which is aggressive against many materials, and the exposure of the entire binder liquid supply system to liquid chloroform, and the handling of chloroform vapor, which is toxic.

Another issue in 3DP has been that 3DP tends to require adjustment of printing parameters to values which are unique to a particular powder and a particular solvent or binder liquid being used. If there are many powders or solvents/binders of interest, then significant effort can be required to determine specific printing parameters, i.e. it can be hard to respond quickly to a change in the formulation.

Porous biostructures made of polymer are disclosed in U.S. Pat. No. 6,454,811, which is incorporated herein by reference. However, those structures were made by dispensing liquid chloroform from a printhead, which resulted in problems of bleeding of dispensed liquid in the powder bed, and so those articles did not have the dimensional resolution of the articles of the current invention. In U.S. Pat. No. 6,454,811, the dispensing of the liquid chloroform included using masks with a continuous stream of liquid chloroform, and the dispensing was performed onto a bed containing particles of PLGA and a leachable porogen. While the printed articles of the '811 patent (after leaching of the porogen) had a high porosity such as 90%, they were still basically rigid and could not undergo any significant deformation without breaking. It is likely that the rigidity was largely due to the material properties of PLGA. Nevertheless, if any such article were able to be made so that it were squeezable, that might open up additional surgical applications.

As far as fields other than three-dimensional printing, and not considered to be prior art to inventions disclosed herein, in printing systems which involve toner powders, such as electrophotographic, electrographic, or magnetographic imaging systems, it is known to use solvent vapor fixing (or solvating) as a way to permanently fix the toner powders to the paper, as an alternative to the commonly used methods which involve heat. U.S. Pat. No. 5,834,150 discloses using environmentally acceptable halogenated hydrocarbons for this purpose. However, the use in that patent was to create two-dimensional images, not three-dimensional structures. Solvent vapor fusing has also been used in other applications such as preparation of dental preforms using the vapor of liquid methyl methacrylate monomer in conjunction with acrylic cements, as described in U.S. Pat. No. 5,336,700. However, this has not extended to three-dimensional printing, nor has it involved leaching of a porogen for creation and control of pores. U.S. Pat. No. 5,171,834 discloses molding a part and then exposing it to solvent vapors.

Accordingly, it would be desirable to be able to achieve the best possible dimensional resolution in polymeric parts which have the geometric complexity that requires the use of 3DP. It would be desirable to minimize bleeding during 3DP such as by printing at a low saturation parameter. It would be desirable to minimize the handling of chloroform and similar aggressive solvents and the exposure of machine parts to such solvents. It would be desirable to provide control of porosity. It would be desirable to incorporate multiple material compositions in articles made of organic-solvent-soluble materials. It would be desirable to make polymeric articles by 3DP without having to spend effort adjusting the printing parameters for changes of polymer or binder formulation.

In general, for porous polymeric articles, it would be desirable to be able to make those articles with good control over the size and shape of the porosity, especially at large porosity fractions.

It would be desirable to make a porous article made at least partly of polymer, which may include internal features, which is capable of undergoing significant elastic deformation without breaking. Such squeezability might make surgical installation easier, reduce the need for on-the-spot shaping during surgery, maintain contact pressure against neighboring tissue to promote tissue integration and ingrowth, etc.

BRIEF SUMMARY

Inventions disclosed herein include methods of manufacturing an article using three-dimensional printing for a portion of the manufacturing. The methods include three-dimensionally printing onto a powder bed which contains both organic solvent-soluable particles and organic-solvent-insoluble particles. The organic-solvent-insoluble particles may include water-soluble particles which may be selected for properties such as particle size and may include more than one substance. The organic-solvent-insoluble particles may further comprise at least one substantially insoluble substance such as a member of the calcium phosphate family. Printing may be done using an aqueous binder liquid. After removal of unbound powder, the preform may be exposed to the vapor of an organic solvent which causes the particles of organic-soluble-polymer to fuse to each other. This may further be followed by dissolving out the water-soluble particles, if such particles were present in the powder. Solvent vapor fusing together with the use of porogen particles may also be used in manufacturing methods other than 3DP.

Inventions also disclosed herein include articles which may be produced by the described methods. Among other features, the articles can be characterized by a high porosity and by an ability to undergo large deformations without breaking, and by at least partial springback from such deformation, at least when made of appropriate polymer. The springback may be substantially instantaneous or may be time-dependent involving a time period of at least several seconds.

Article of Manufacture

Figure 2A:
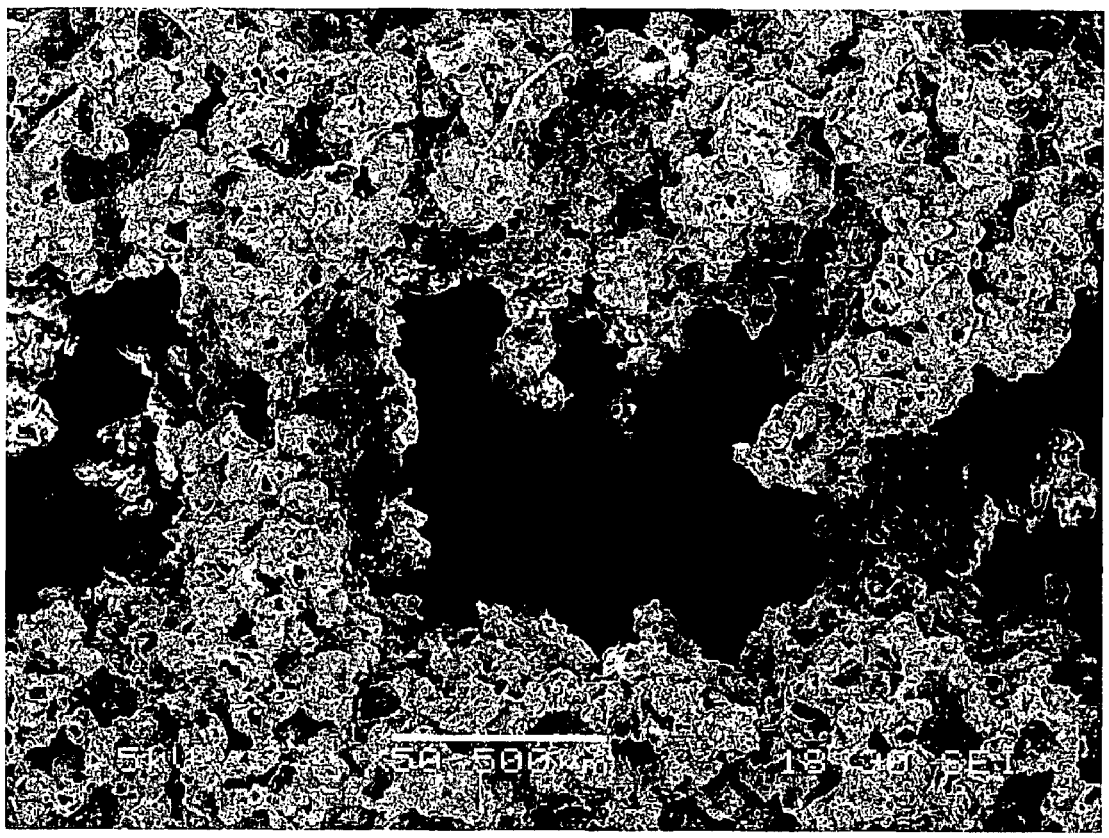
FIG. 2A is a digital image of a scanning electromicrograph of an article made by a vapor film forming method of an invention hereof having a powder mixture of 80% sugar and 20% PCL at a magnification of ×50.
Figure 2B:
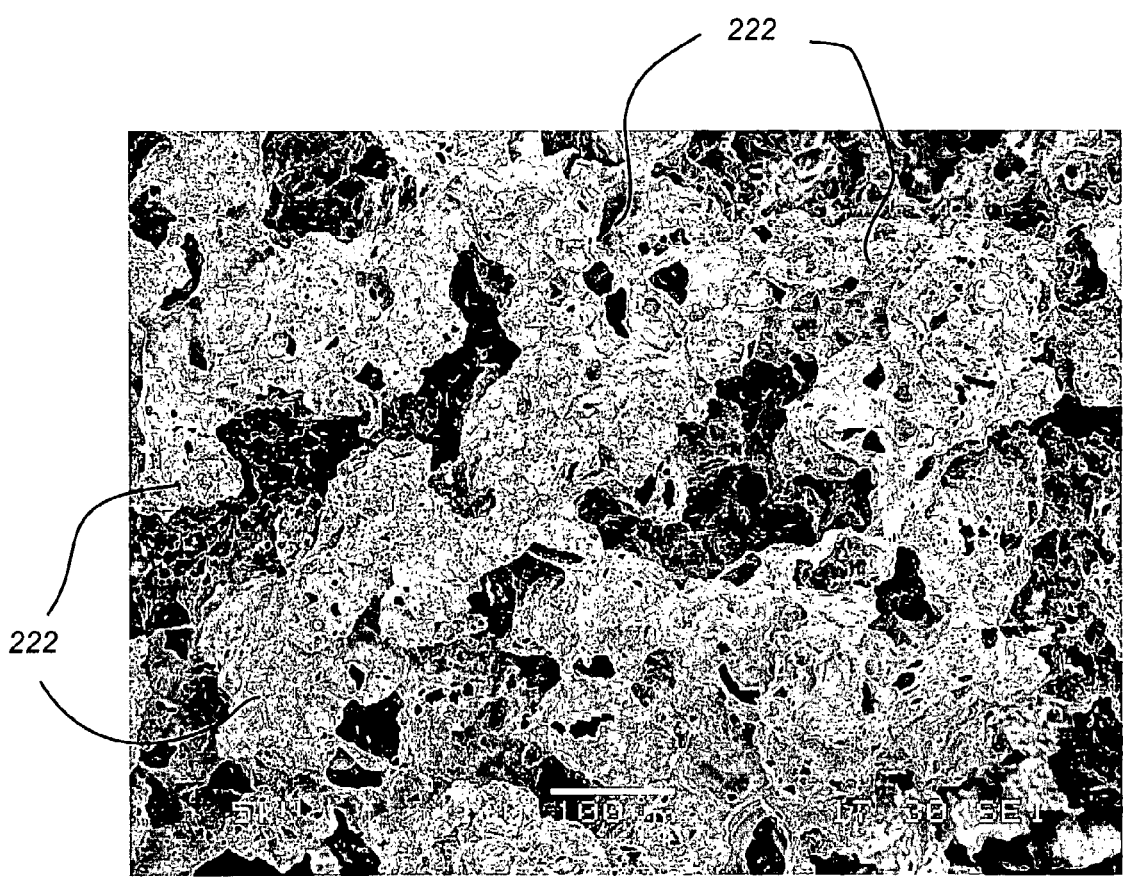
FIG. 2B is a digital image of the article shown in FIG. 2A, at a magnification of ×160.
Figure 2C:
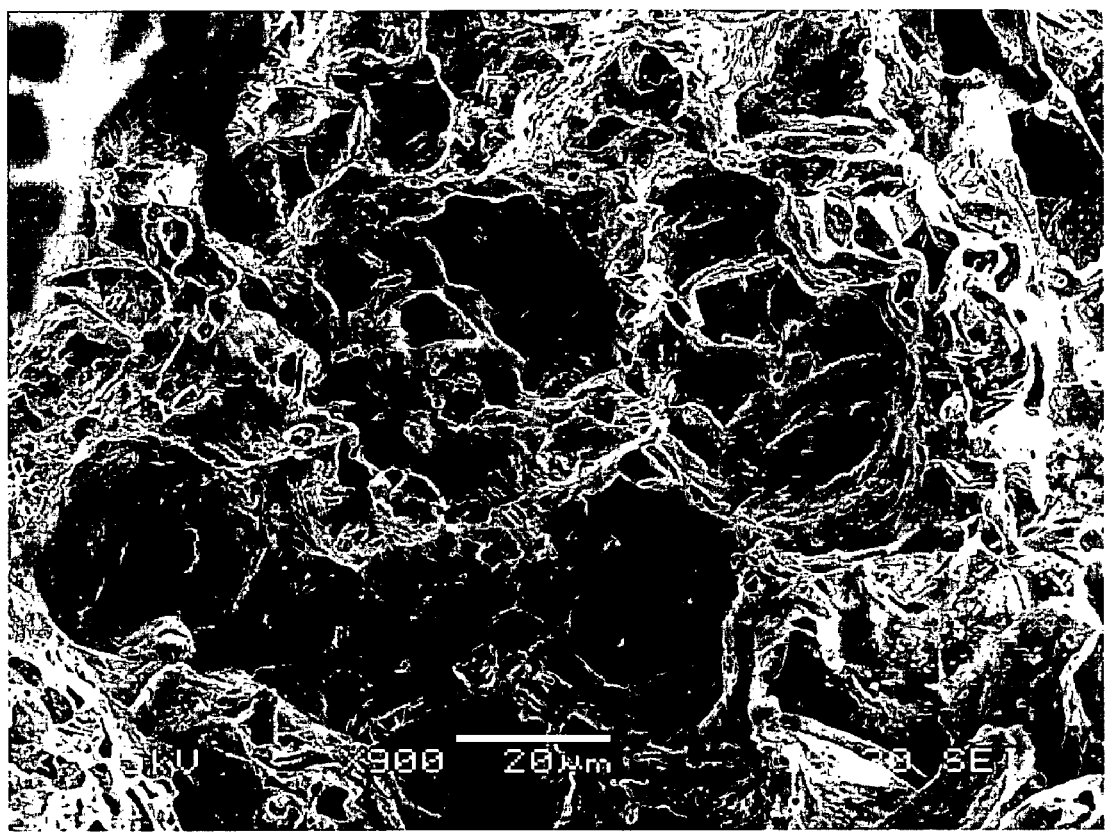
FIG. 2C is a digital image of the article shown in FIG. 2A, at a magnification of ×900.
Figure 3A:
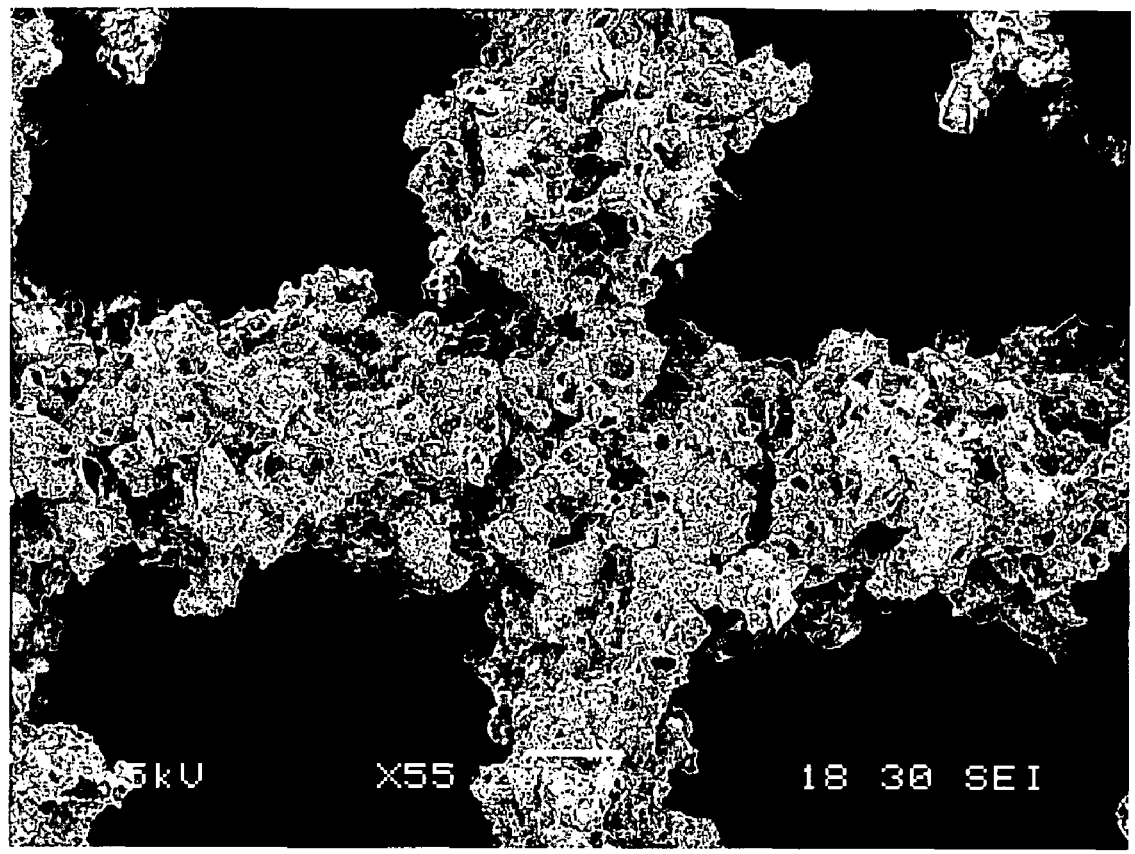
FIG. 3A is a digital image of a scanning electromicrograph of an article made by a vapor film forming method of an invention hereof having a powder mixture of 70% sugar and 30% PCL at a magnification of ×55.
Figure 3B:
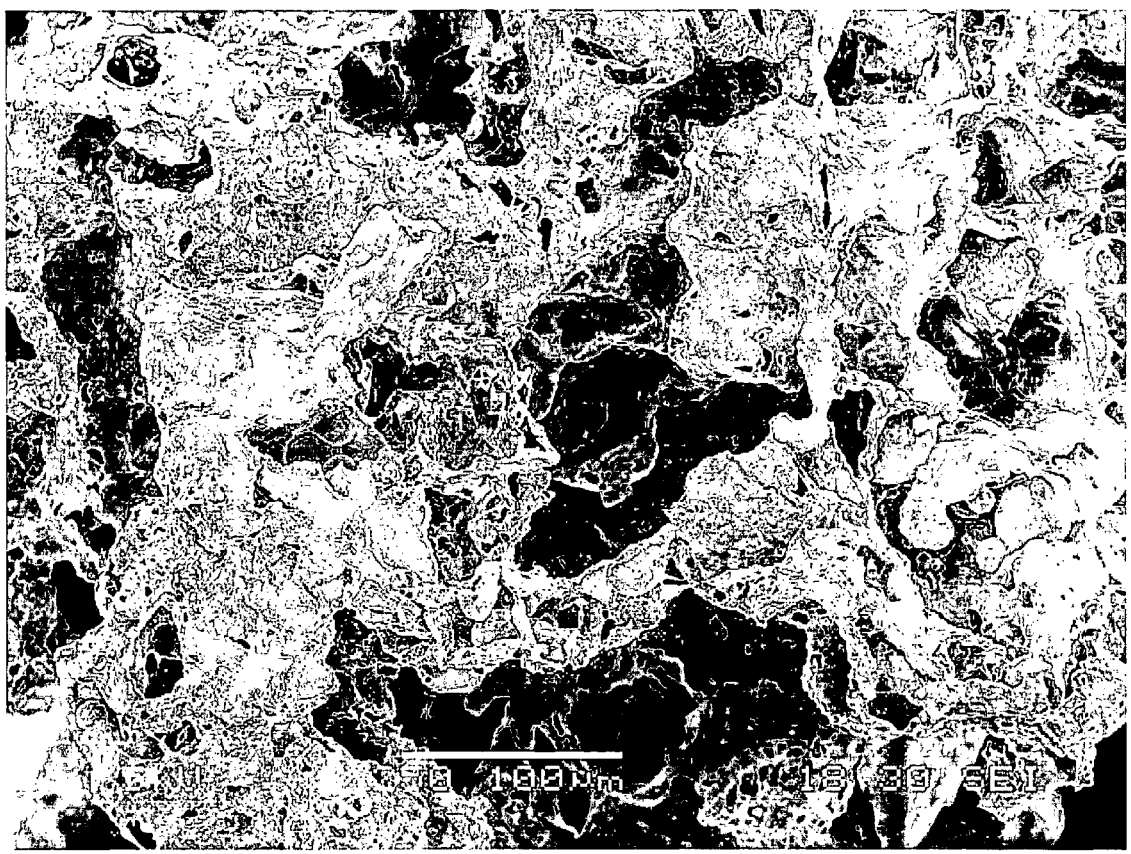
FIG. 3B is a digital image of the article shown in FIG. 3A, at a magnification of ×250.
Figure 3C:
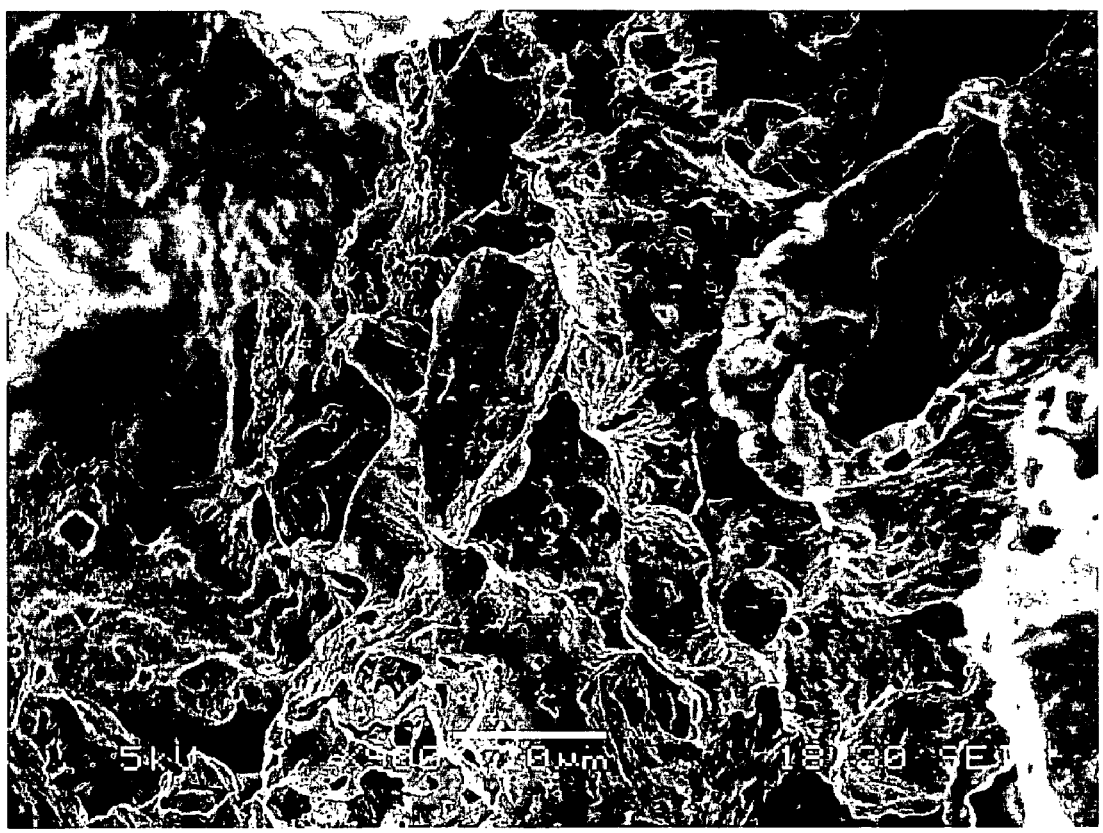
FIG. 3C is a digital image of the article shown in FIG. 3A, at a magnification of ×900.

In terms of geometry or morphology, an article of an invention hereof comprises a network or porous structure comprising an organic-solvent-soluble substance(s) which may be a polymer. At a size scale under approximately 100 micrometers, the article may be characterized by a geometry or morphology as having a basic structure, in which substantially all of the polymer has the form of a film which is somewhat randomly crinkled and perforated but is otherwise continuous. This is illustrated in FIGS. 2A, 2B and 2C, representing magnifications of ×50, ×160 and ×900, respectively. In this geometry or morphology, there is substantially no presence of identifiable polymer particles.

Figure 4A:
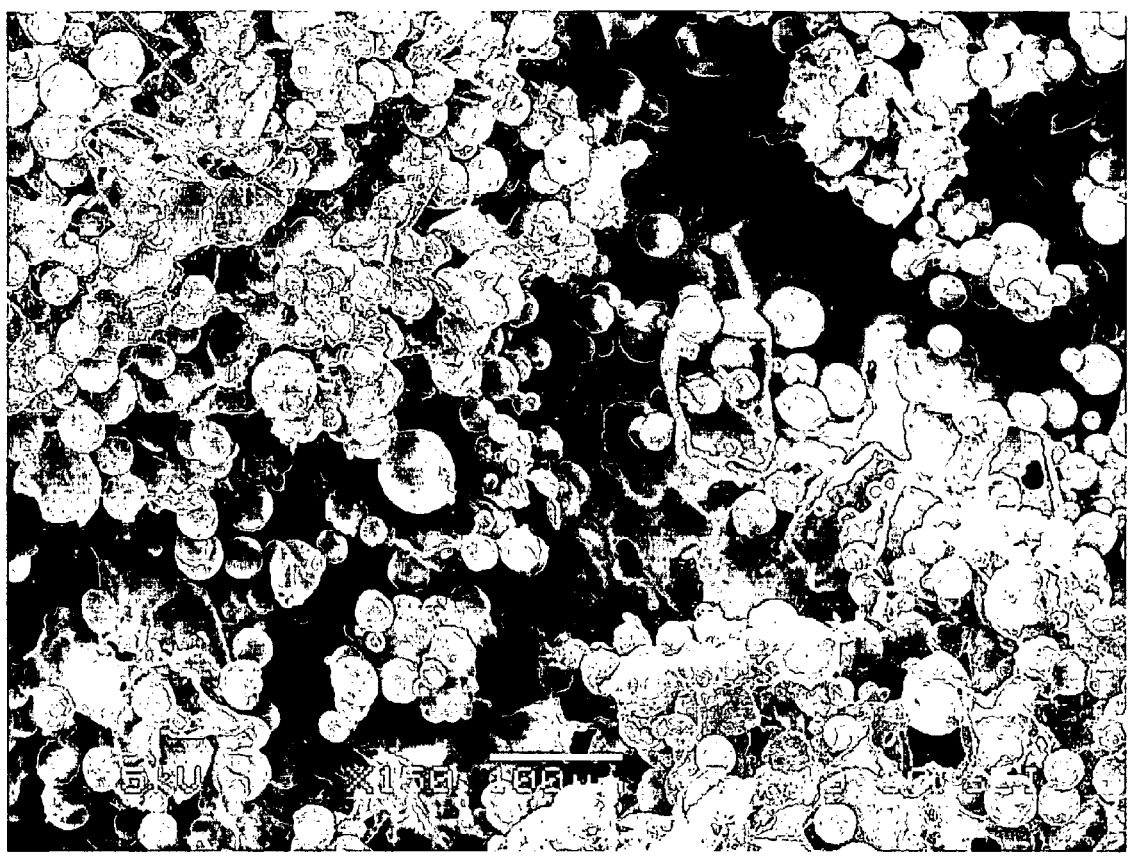
FIG. 4A is a digital image of a scanning electromicrograph of an article made by a prior art method printing liquid chloroform and a powder mixture of 80% NaCl and 20% PCL at a magnification of ×150.
Figure 4B:
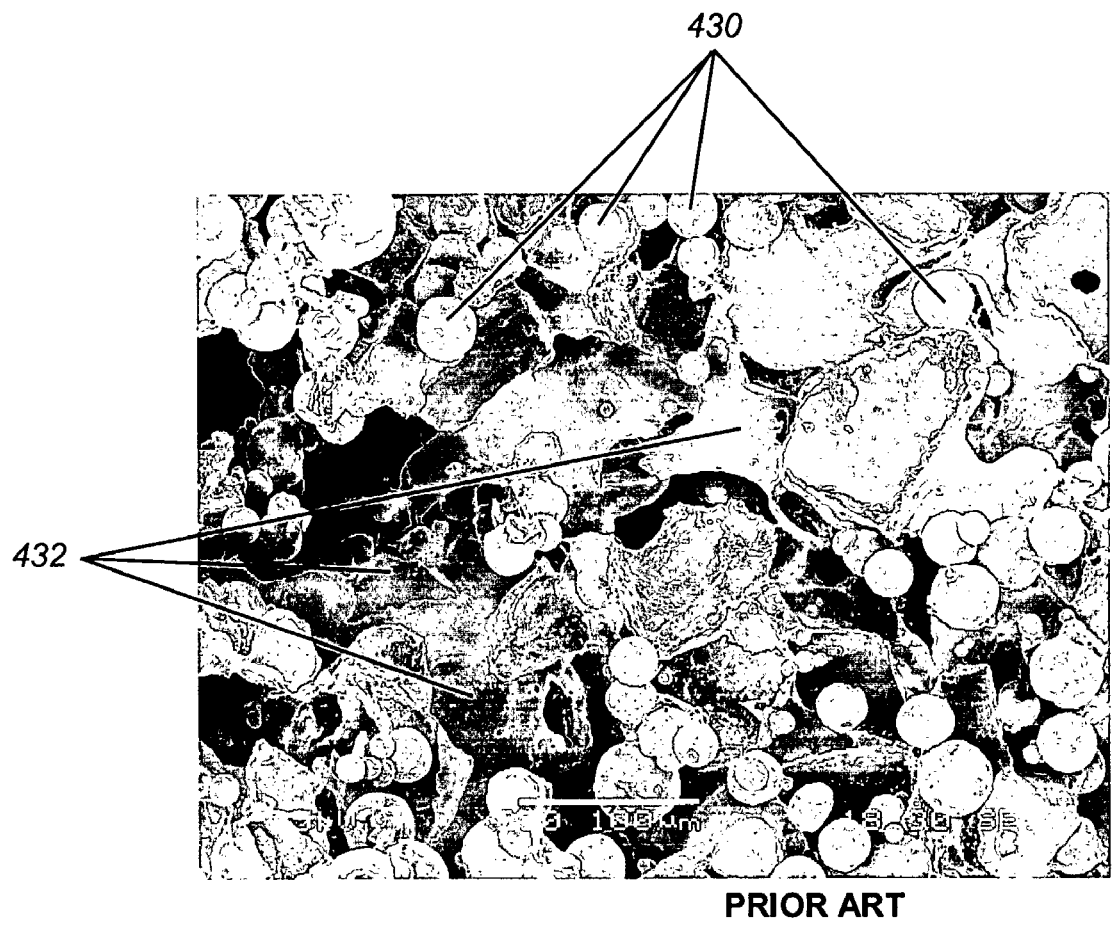
FIG. 4B is a digital image of the prior art article shown in FIG. 4A, at a magnification of ×250.

This can be contrasted with the microstructure of conventional structures made by 3DP, shown in FIG. 4B. In the conventional structure there is some basic polymeric structure which is in the form of a crinkled film, but in addition, there can be seen some approximately spherical powder particles which are attached to the basic structure but which are not fully fused into the basic polymeric structure.

An article of an invention disclosed herein can be characterized by a high porosity such as greater than 80% in regions which do contain the network (i.e., are not macroscopic polymer-free features). On a larger size scale, an article of an invention disclosed herein can have macrochannels and other polymer-free macroscopic internal features with cross-sectional dimensions as small as approximately 100 micrometers, or larger cross-sectional dimensions. Examples of articles according to a present invention are shown in FIGS. 5A-5H, which are, respectively, as identified above.

In terms of materials, the organic-solvent-soluble network in an article can comprise a polymer such as polycaprolactone, and can comprise a comb polymer. Polymethylmethacrylate and the PLGA family are also polymers which could be used. The organic-solvent-soluble substance in the article can be biologically resorbable if desired. The organic-solvent-soluble substance can be the same everywhere in the biostructure or it can be different at different places in the biostructure.

The article can also comprise an insoluble (i.e., insoluble in substantially any solvent) material, which may exist in the form of particles of the insoluble material which are at least partly held by the polymeric structure. The organic-solvent-insoluble substance which is present in the finished article can be a member of the calcium phosphate family, so as to be useful for bone growth applications. For example, the insoluble substance can be tricalcium phosphate, which is resorbable. Composition of the insoluble material(s) also can vary from place to place within the article.

As a result of at least some of the described attributes (the crinkled perforated film microstructure, the macrostructure, and the mechanical properties of polymers such as polycaprolactone), an article of an invention disclosed herein can have mechanical properties such that the article can undergo a large deformation and display at least some resilience (springback). For example, an article of a disclosed invention, when made from polycaprolactone, can be elastically deformed to strains of at least 10% and can then spring at least partway back to its original shape and dimensions. The springback may be substantially instantaneous or may be time-dependent involving a time period of at least several seconds. The polymer network in the finished article has a geometry which is tortuous and comprises crinkled perforated films. This, together with the material properties of polymers such as polycaprolactone is believed to be related to the ability of the article to elastically deform to rather large strains. The possible time-dependent springback is believed to be due to similar factors.

Method of Manufacturing

Figure 6:
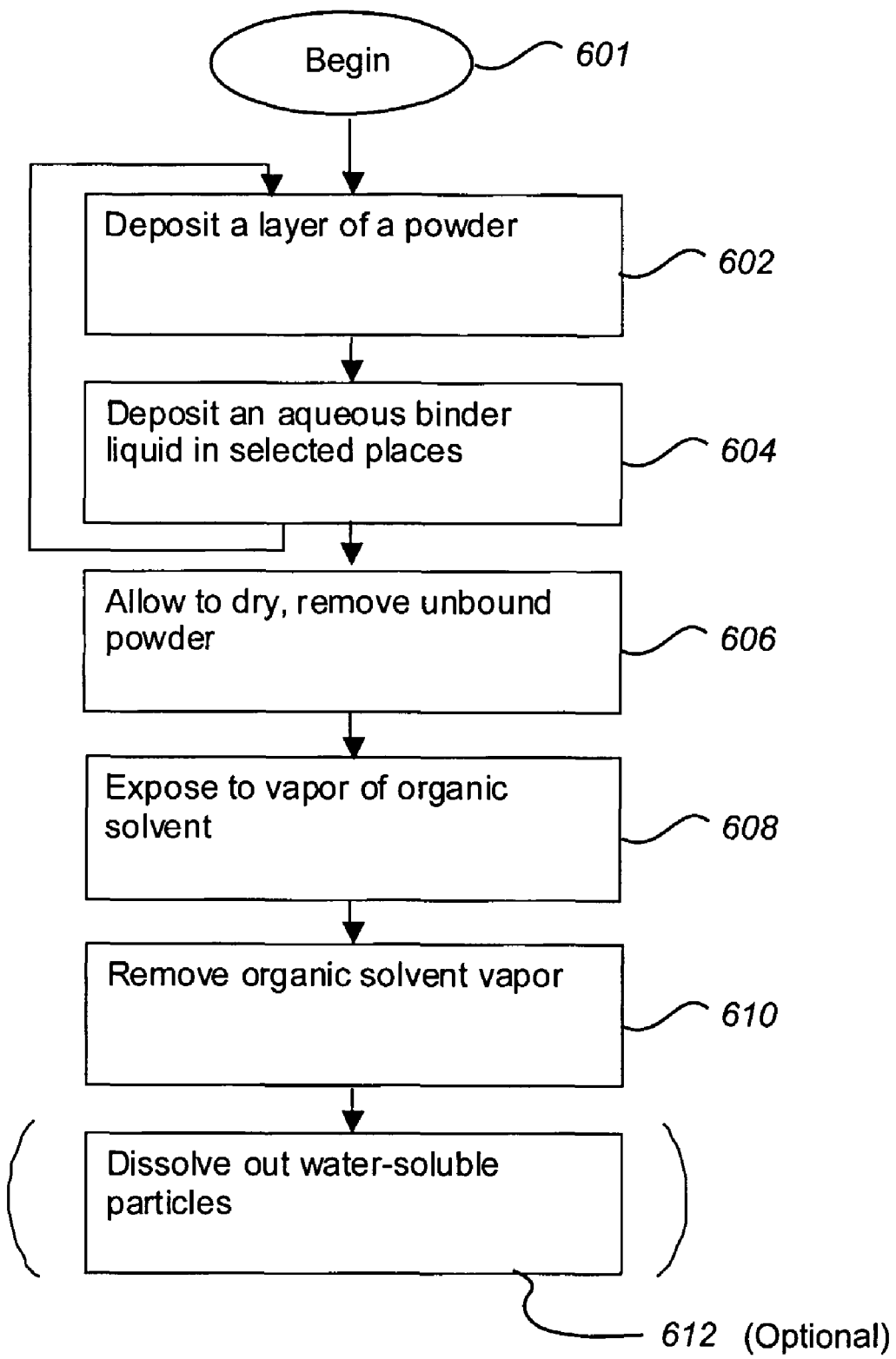
FIG. 6 is a schematic flow chart showing steps of a 3D Printing vapor filming embodiment of a method of an invention hereof.

Inventions disclosed herein include methods of manufacturing which include solvent vapor fusing and may include using three-dimensional printing for a portion of the manufacturing process. The manufacturing process starting with three-dimensional printing is illustrated in the FIG. 6. The method of manufacturing a biostructure may include the following steps as illustrated in FIG. 6.

A layer of powder may be deposited 602, such as by roller spreading or other suitable means. This powder may comprise particles of at least two substances. The powder may comprise particles of at least one substance, designated an organic-solvent-soluble substance, which is soluble in an organic solvent of interest but which has a low or negligible solubility in water. Additionally, the powder may comprise particles of an organic-solvent-insoluble substance. Choices regarding the organic-solvent-insoluble substance(s), which may comprise water-soluble substances or substances which are essentially insoluble in any solvent, or both types of substances, are described elsewhere herein.

Organic-solvent-soluble substances of interest include essentially any polymer which may be of interest for biological applications and which is soluble in a suitable organic solvent. Specific polymers of interest include polycaprolactone and comb polymers, and polymethylmethacrylate and members of the poly lactic co-glycolic acid (PLGA) family. Polycaprolactone (Sigma-Aldrich, St. Louis, Mo.) may, for example, have a molecular weight of approximately 60,000 to 65,000 Daltons. What is referred to here as an organic-solvent-soluble substance could be a mixture of more than one organic-solvent-soluble substances, either existing as discrete particles blended among each other or commingled within individual particles. The organic-solvent-soluble substance can be the same everywhere in the biostructure or it can be different at different places in the biostructure. This can be accomplished, for example, by spreading different powders in different layers of the three-dimensional printing process.

In defining the terms organic-solvent-soluble and organic-solvent-insoluble, reference may be made to an organic solvent of interest for a particular substance or application. An organic solvent of particular interest is chloroform ($CHCl_3$), because of the large number of substances which chloroform is capable of dissolving. Other chlorinated hydrocarbons are similarly of interest, as are still other organic solvents. It is also possible that supercritical carbon dioxide can be considered as a solvent capable of causing the particles of polymer (organic-solvent-soluble substance) to solvent-fuse.

The proportions of the various components of the powder may be chosen with a view toward how they will form structures, such as which types of particles (if any) might be trapped within structures formed by the other substance.

After the depositing of a layer of the described powder, a next step may be to deposit 604 onto the powder in selected places an aqueous binder liquid suitable to join particles to other particles. The aqueous binder liquid can be either pure water or water with a binder substance dissolved in it. As described elsewhere herein, there are two possible ways in which an aqueous binder liquid can bind powder particles.

As is known in the art, there is a substantial base of experience in deposition of an aqueous binder liquid. Of particular interest in the practice of the present invention is limiting the spread of the deposited binder liquid in the powder, so as to produce the sharpest possible printed features. One way to do this is to deposit the aqueous binder liquid using a relatively low value of the saturation parameter.

Parameters which influence printing may be summarized as a quantity called the saturation parameter. If printing is performed with discrete drops, each drop is associated with a voxel (unit volume) of powder that may be considered to have the shape of a rectangular prism. The dimensions of the voxel are the drop-to-drop spacing which may be called delta x, the line-to-line spacing which may be called delta y, and the thickness of the powder layer, which may be called delta z. The voxel contains within it a total volume given by (delta x)*(delta y)*(delta z). Within the voxel is a certain amount of empty volume representing the space between powder particles, i.e., space not occupied by powder particles, given by (1−pf)*(delta x)*(delta y)*(delta z), where pf is the powder packing fraction. The ratio of the dispensed droplet volume to the empty volume in the voxel is the saturation parameter. The drop volume may be represented by Vd. The saturation parameter is given by Vd/((1−pf)*(delta x)*(delta y)*(delta z)).

In the practice of the present invention, the deposition of the aqueous binder liquid can be done at a saturation parameter as small as 10% to 20%. This range is substantially smaller than what is used in most three-dimensional printing, and this is useful in improving the dimensional resolution of the final product.

The two steps of powder layer deposition and binder liquid deposition onto the powder layer can be repeated as many times as needed, with appropriate deposition patterns at each layer, to produce a desired geometry. It is not necessary that the powder which is spread in any given layer be the same as the powder which is spread in other layers. The powder could differ in its composition, in particle sizes and particle size distributions, and in other respects. In regard to composition, the powder in a given layer in the 3DP process could have a different organic-solvent-soluble substance(s) from what is in other layers. Similarly, compared to other layers, the powder in a given layer could have a different organic-solvent-insoluble substance or substances or could have more or fewer of such substances.

Next, the printed powder bed can be allowed 606 to dry as needed and then unbound powder can be removed, resulting in a preform. At this point the particles of organic-solvent-soluble substance would not be joined directly to each other because only an organic solvent would be able to cause that, and the article has not yet been exposed to any organic solvent during this process. At this point some particles would be joined to each other through the solidification of one or more substances which are soluble in water, which is the base liquid of the aqueous binder liquid. It is possible that particles be joined to each other through a combination of solidification of whatever binder substance (if any) may have been dissolved in the binder liquid, or through the at least partial dissolution of water-soluble particles in the powder bed followed by resolidification.

It is believed, although it is intended not to be restricted to this explanation, that the structure of the water-soluble particles, together with any binder substance that may have been dissolved in the binder liquid (if any such binder substance was used), forms a structure which will keep the organic-solvent-soluble particles in position while those particles are not yet joined to each other. Similarly, it is believed that if any insoluble particles are present, this structure will keep the insoluble particles in position during this stage of manufacturing.

Next, the preform can be exposed 608 to vapor of an organic solvent in which the organic-solvent-soluble particles are soluble. This can be done at a suitable vapor concentration and for a suitable time and for suitable values of any other relevant parameters, to cause at least some joining of organic-solvent-soluble particles to other organic-solvent-soluble particles. For example, when liquid chloroform is enclosed in a closed container initially containing air, evaporation of liquid chloroform will occur until the partial pressure of chloroform vapor inside the container reaches a saturation value which is dependent only on temperature, and at that point the concentration of chloroform vapor will remain at a steady value. Achieving this condition requires only that a sufficient amount of liquid chloroform be initially provided. Since a typical procedure would involve enclosing more than this minimum amount of liquid inside the closed container, the article to be solvent-vapor-fused may be supported in such a way that the article does not contact the liquid chloroform region and yet is well exposed to chloroform vapor.

For relatively large parts, where the internal regions are relatively distant from external surfaces, it may be helpful to use a vacuum container in which the organic solvent is introduced and achieves partial pressure, instantly filling interior regions, to eliminate or reduce any propensity for surface capillary stress cracks, which can result in a saturated air environment where migration of solvent vapor by diffusion is retarded.

It is believed, although it is intended not to be restricted to this explanation, that particles of the organic-solvent-soluble substance (such as a polymer) absorb the organic solvent even from a vapor state and thereby become dissolved or at least softened. For example, it is believed that polycaprolactone can absorb chloroform vapor to an extent of 3 to 5%. In this regard, since many polymers are not crystalline solids anyway, it is helpful to think of those polymers as highly viscous liquids, which are merely being diluted to a lower viscosity by the chloroform or other organic solvent vapor. It is believed that the presence of chloroform lowers the effective glass transition temperature of the polymer.

It is further believed that when the particles of organic-solvent-soluble substance become dissolved or at least softened, they deform, flow or spread and it is believed that the pre-existing structure formed by the water-based binder liquid provides a surface/structure upon which the organic-solvent-soluble particles can spread when they become soft and will thereby help the organic-solvent-soluble particles find each other and coalesce. It is believed that the dissolved or softened particles of organic-solvent-soluble substance then contact and at least somewhat merge with other particles of the same substance, thereby forming a connected film structure of the organic-solvent-soluble substance.

Figure 7:
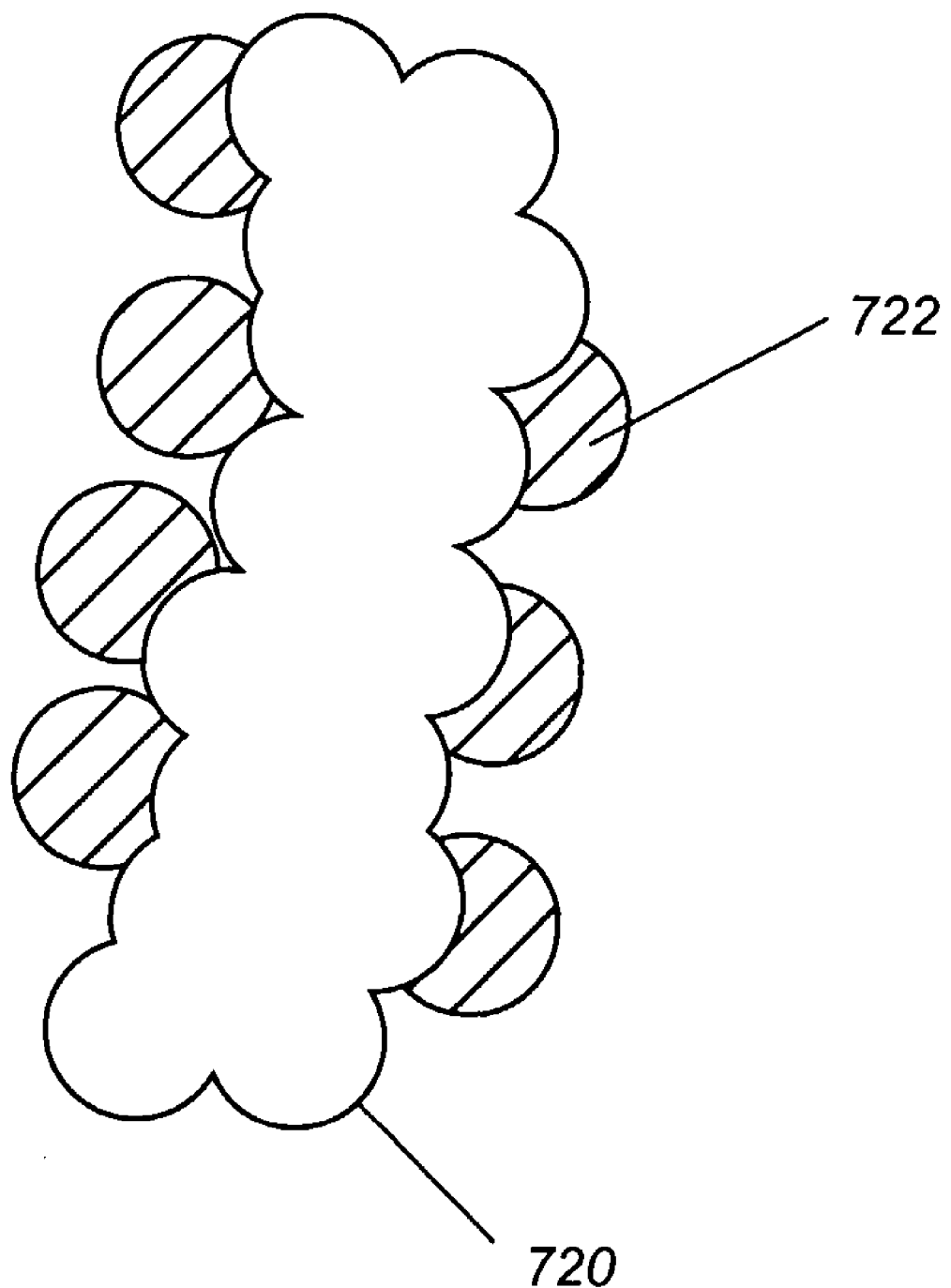
FIG. 7 is a schematic rendition of a cross-section of a preform for use with method inventions hereof, having a first type of particulate material that is adhered to other particles of the same type, shown unshaded, to which are also stuck a second type of particles (shaded).
Figure 8:
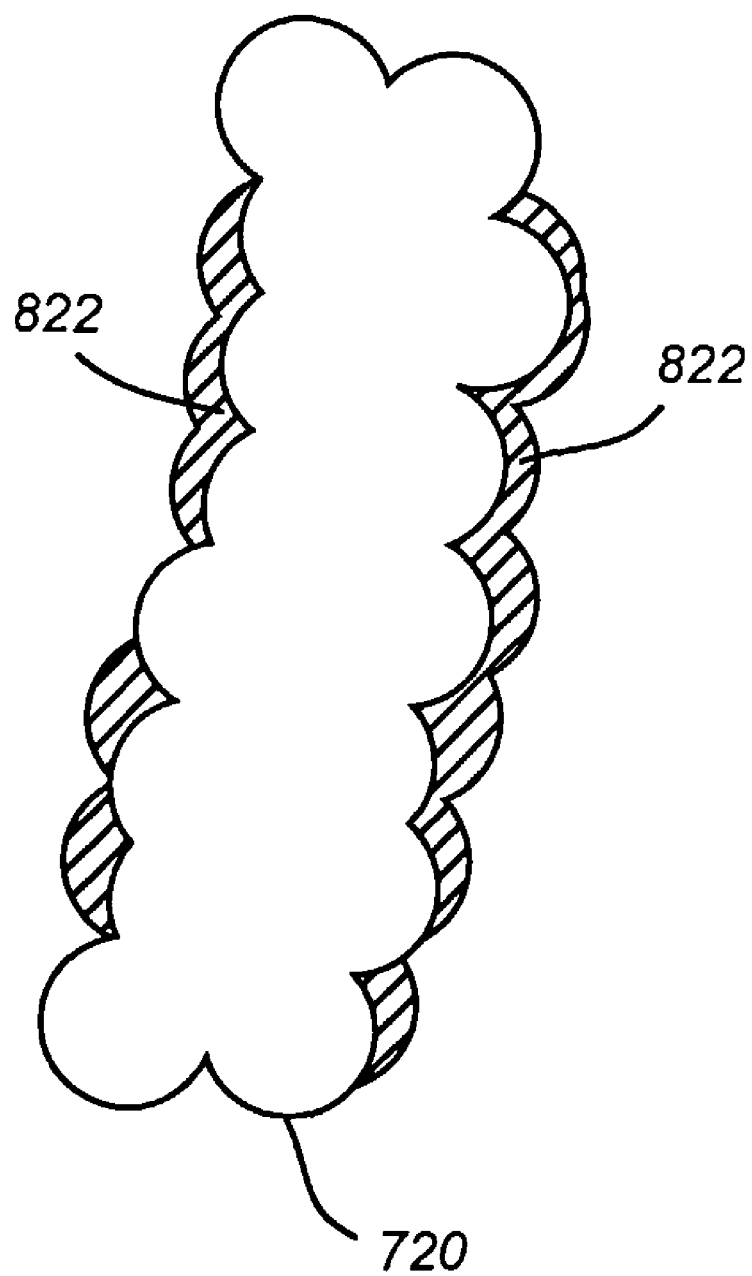
FIG. 8 is a schematic rendition of a cross-section of the preform shown in FIG. F, where the second type of bound structure particulate material has been filmed and flowed to follow closely the contours of the adhered structure of the first particulate material.
Figure 9:
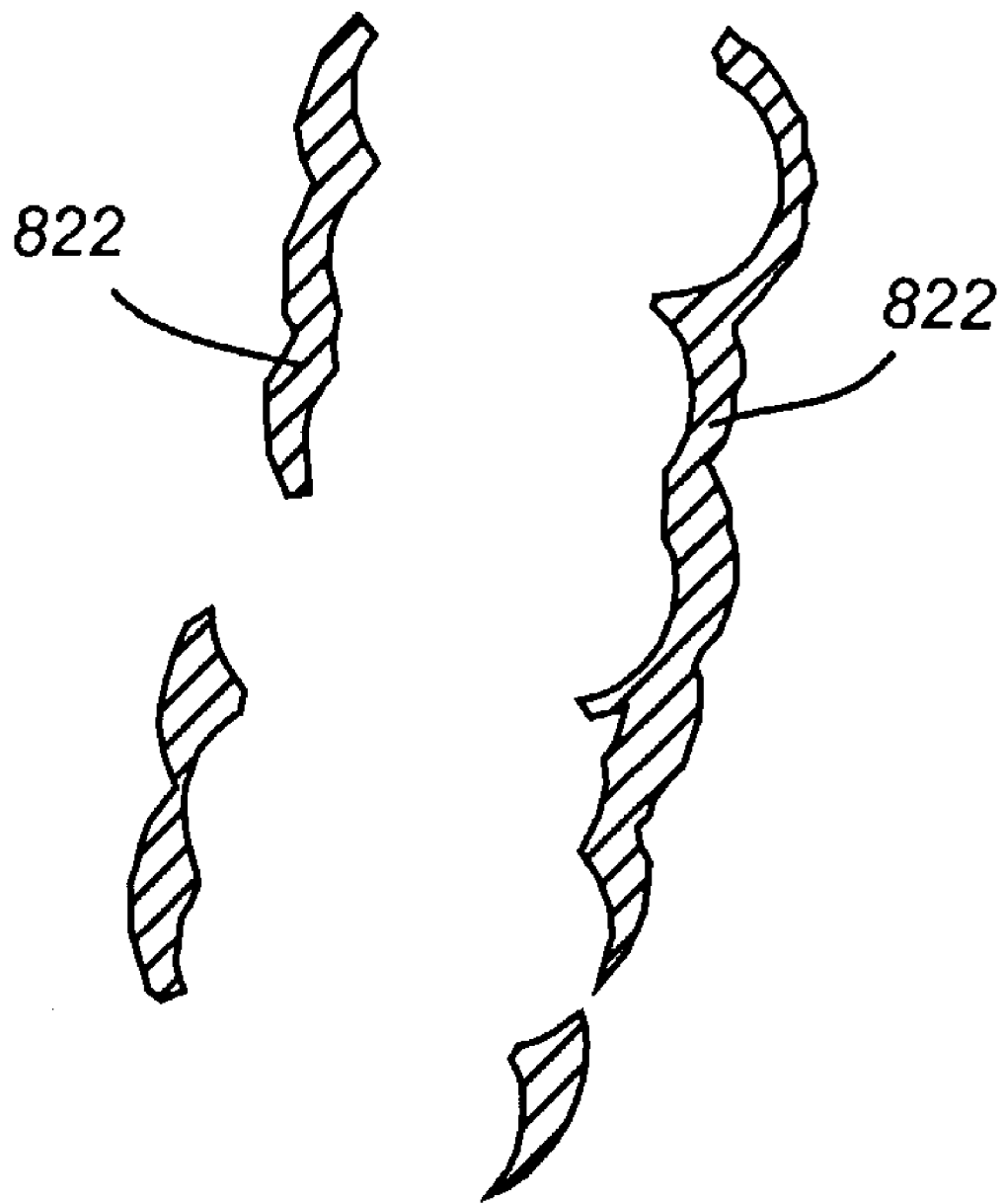
FIG. 9 is a schematic rendition of a cross-section of a preform such as shown in FIG. 8, in which the first type of particulate material has been removed, such as by a solvent, and the second type of material forming films remains.

The process is further illustrated schematically in the FIGS. 7, 8 and 9. FIG. 7 shows what the article looks like after printing with the aqueous binder liquid and drying, before solvent vapor fusing. At this stage, the organic-solvent-insoluble particles 720, which are white, are shown fused together such as from dissolution in water followed by resolidification, or from solidification of a binder substance initially dissolved in the binder liquid. Thus, the organic-solvent-insoluble particles 720 form a somewhat continuous structure. The organic-solvent-soluble particles 722, shown shaded, are shown somewhat incorporated into the already-fused structure of the organic-solvent-insoluble particles, but are shown as being separate and distinct from each other because at this stage they have never been exposed to an organic solvent which would make them fuse to each other.

FIG. 8 shows the appearance of the preform after exposure to solvent vapor. It is believed that the former individual particles 722 of organic-solvent-soluble substance have merged into each other and created a sort of film 822 on the surface of the structure formed by the organic-solvent-insoluble substance(s) 720. The morphology of that film 822 is believed to closely follow the morphology of the surface of the structure formed by the organic-solvent-insoluble substance(s) 720.

After this, the preform can be removed 610 from the organic solvent vapor and can be exposed for a sufficient time to conditions of substantially no concentration of organic solvent vapor, so that substantially all of the organic solvent which may have been absorbed into the preform can leave the preform. The films of polymer or organic-solvent-soluble substance will harden. At this point the preform contains both a connected structure 720 of water-soluble substance and a connected structure 822 of organic-solvent-soluble substance, with the two connected structures being intertwined with each other. If insoluble particles (not shown) are present, it is believed that at least some of them can be held in place at least partly by the newly-formed structure 822 of organic-solvent-soluble substance.

At either this stage or a later stage, it is possible that residual organic solvent such as chloroform could further be removed by either a liquid carbon dioxide extraction process or a supercritical carbon dioxide extraction process.

Finally, the preform can be exposed to water under conditions suitable to dissolve out 612 substantially all of the water-soluble material or particles 720. As shown in FIG. 9, this leaves the structure of organic-solvent-soluble substance 822, which may also contain particles of the insoluble substance if such particles were present in the original powder. The structure which remains is illustrated in FIG. 9. (For simplicity, insoluble particles have not been illustrated in these schematic illustrations.)

Water-Soluble Substances

Among the many water-soluble materials that could be used as an organic-solvent-insoluble substance in the described process are sugars and salts. The family of salts includes sodium chloride as well as many other substances. The family of sugars includes sucrose, fructose and lactose, among others. Various combinations of these materials have been used to form the powder for 3DP experiments such as are described elsewhere herein. The choice and proportion of the members of the salt and sugar families can be determined by balancing various properties based on observations.

It has been found that particles of sodium chloride have an ability to absorb a certain amount of moisture before they actually begin to form necks which would join particles to each other. This property may be of some help in limiting the spread of aqueous liquid in the powder bed. The rate of dissolution of sodium chloride in water could be described as moderate among the various substances tried.

Fructose and sucrose exhibit fairly rapid dissolution in water, which can be useful for forming necks joining particles. Lactose exhibits slower dissolution in water, in comparison to fructose and sucrose. This property of slower dissolution can be useful for a different reason. While other substances such as fructose and sucrose may be significantly involved in the dissolution/resolidification process based on water, the lactose particles may continue to exist throughout that process in a fairly intact manner.

It is thus likely that the lactose particles as originally supplied in the powder may still have a significant presence at the time the solvent-vapor-softened polymer flows to attain its final state. For example, the structure after aqueous binding may comprise lactose particles joined to each other by necks which are made primarily of one of the other, more water-soluble sugars. Thus the lactose particles as originally supplied in the powder may significantly determine the size and size distribution of the pores which exist in the final product. Achieving this situation may be helped if the amount of relatively quickly-dissolving sugar, which is intended to be in the necks, is somewhat smaller than the amount of lactose (because if the particles are to retain a prominent shape, the necks have to have smaller volume than the particles). It is believed that this gives more control over the porosity of the resolidified structure than would be available from dissolution/resolidification with just a single substance in the powder bed.

However, it is still completely possible to ultimately remove the lactose particles from the finished product by dissolution in water, because there are no significant time limits associated with the dissolution/removal (leaching) process. There is no problem soaking the product in water for a sufficient time to remove lactose. Of course, still other water-soluble materials could also be used as components of the powder. The proportions of these substances can be chosen to achieve the desired characteristics of porosity, etc. in the finished product. Any number of these substances can be included in the powder, and the particle size or particle size distribution of each type of particle can be different if desired. Any of these parameters could be varied from layer to layer in the 3DP process.

In addition, although this is optional, the powder may further comprise particles of yet another substance which may have low solubility or substantially no solubility in water and also have low solubility or substantially no solubility in organic solvents. This substance may be designated the insoluble substance. Examples of such insoluble substances include ceramics such as bioceramics including members of the calcium phosphate family such as tricalcium phosphate, such as substances which are useful for supporting the ingrowth of bone. The choice of whether to include an insoluble material such as tricalcium phosphate depends on whether that material is desired in the finished product.

The particles of the water-soluble substance can have a respective particle size and particle size distribution, and the particles of the organic-solvent-soluble substance can have their own respective size and size distribution, which may be the same as or different from the size and size distribution of the water-soluble particles. Furthermore, if insoluble particles are present, those particles may have their own respective size and size distribution which can have any relation to the other two particle sizes and size distributions. Any of these can be varied from layer to layer in the 3DP process.

Sterilization may be accomplished by any of several means and sequences in relation to the overall manufacturing process. The overall manufacturing process may include terminal sterilization, such as by electron beam irradiation, gamma radiation, ethylene oxide, or other means.

After the completion of the described manufacturing steps, the biostructure can be infused with additional substances.

EXAMPLES

The inventions are further described but are in no way limited by the following non-limiting Examples.

Example 1

This Example compares the microstructure of polymer structures which were 3D-printed using the water printing solvent vapor fusing of the present invention against the microstructure of polymer structures which were 3D-printed using conventional dispensing of liquid chloroform onto a powder bed operating using the dissolution/resolidification mechanism. Both powderbeds contained a water-soluble porogen for later leaching out as an aid to creating porosity in the finished biostructure.

Figure 4C:
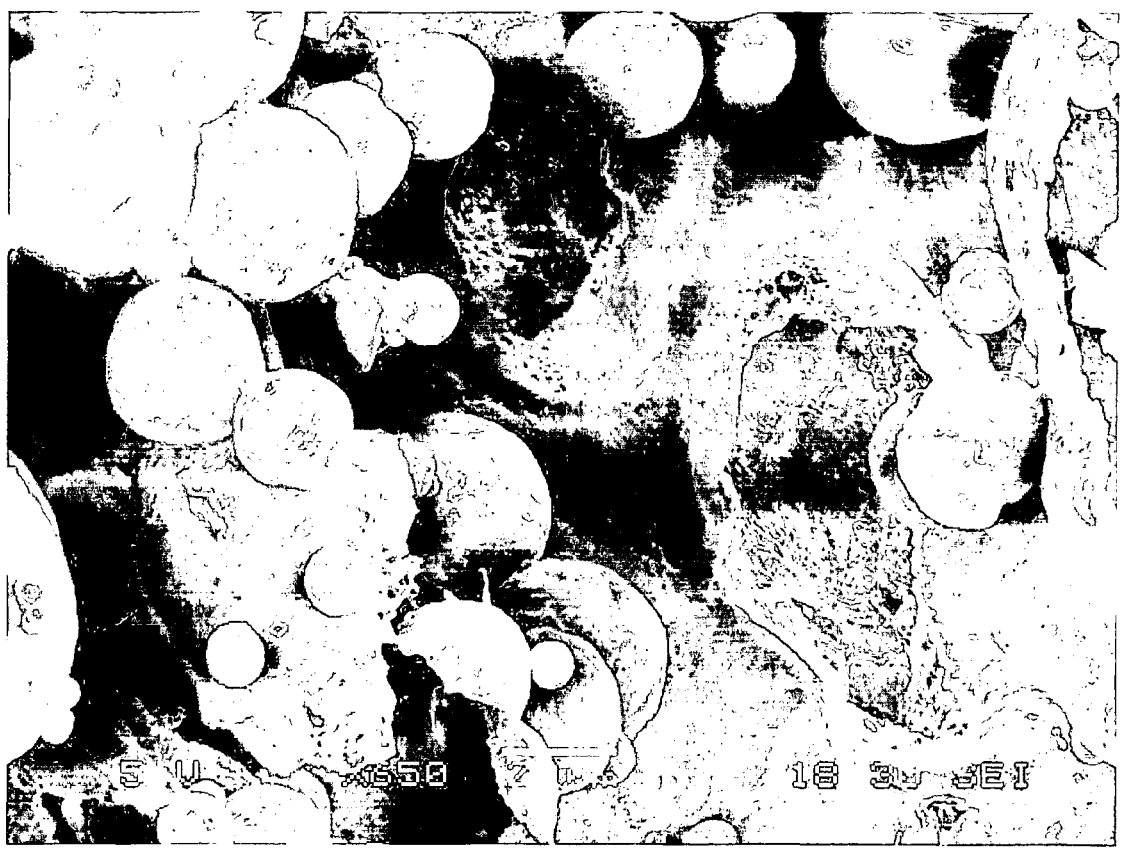
FIG. 4C is a digital image of the prior art article shown in FIG. 4A, at a magnification of ×650.
Figure 5A:
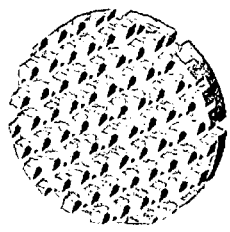
FIG. 5A representing a first waffle pattern, with 0.6 mm pores and 0.6 mm posts.
Figure 5B:
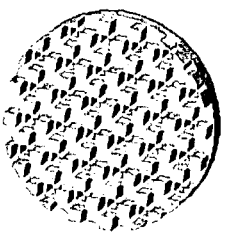
FIG. 5B representing a second waffle pattern, with 0.6 mm pores and 0.6 mm posts.
Figure 5C:
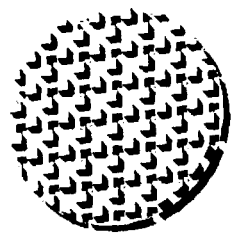
FIG. 5C representing a first waffle pattern, with 0.5 mm pores and 0.5 mm posts.
Figure 5D:
FIG. 5D representing an assembly with three first waffle pattern elements, with 1 mm posts and two second waffle pattern elements with 0.5 mm posts.
Figure 5E:
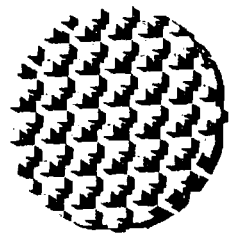
FIG. 5E representing a second waffle pattern, with 1 mm pores and 0.5 mm posts.
Figure 5F:
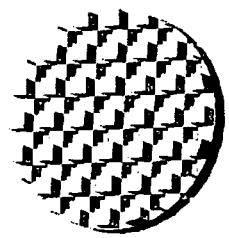
FIG. 5F representing a second waffle pattern, with 0.75 mm pores and posts (50%).
Figure 5G:
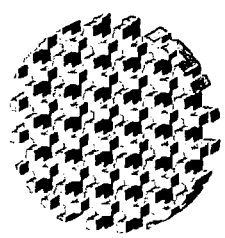
FIG. 5G representing a first waffle pattern, with 1 mm pores and 0.5 mm posts.
Figure 5H:
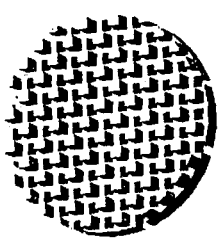
FIG. 5H representing a second waffle pattern, with 0.5 mm pores and 0.5 mm posts.

FIGS. 4A, 4B and 4C illustrate the microstructure of the structure made by conventional 3DP with dispensed liquid chloroform. The powder used in this case was 80:20 NaCl:PCL, magnifications are ×150, ×250 and ×650, respectively.

There is some basic polymeric structure, which has the form of a film 432 (FIG. 4B) which is somewhat randomly crinkled and perforated but is somewhat continuous. This basic polymeric structure is believed to come from polymer material which dissolved completely or almost completely in the liquid chloroform, and which then resolidified in the form shown upon evaporation of the chloroform. It is believed that the structure of what is seen as the basic polymeric structure probably was determined by the leachable particles which occupied some of the space in the figure during the time that dissolution and resolidification were occurring. In addition, in this figure there can be seen some approximately spherical powder particles 430 which are attached to the basic structure but which are not fully fused into the basic polymeric structure 432. It is believed that during the processes of dissolution, possible liquid migration in the powder bed, and resolidification, such particles became wetted by the chloroform liquid enough to become attached to the basic polymeric structure upon evaporation of the chloroform. However, those particles never became sufficiently wetted to fully dissolve such that they would resolidify in a manner integral with the structure.

The microstructure of an article of an invention disclosed herein is illustrated in FIGS. 2A, 2B and 2C. (This was made by water printing solvent fusing according to the present invention.) The powder used in this case was 80:20 Sucrose:PCL, The liquid dispensed during the 3DP process was pure water. FIGS. 2A, 2B and 2C show such an article at magnifications of ×50, ×160 and ×900, respectively.

In the microstructure made by a present invention, substantially all of the polymer has the morphology of a film 222 (FIG. 2B) which is somewhat randomly crinkled and perforated but is somewhat continuous. This basic polymeric structure is believed to come from polymer material which substantially dissolved or softened upon exposure to the chloroform vapor, and which then resolidified in the form shown upon removal of the chloroform. It is believed that the structure of what is seen as the basic polymeric structure probably closely follows the surface shape of the leachable (water-soluble) particles which occupied some of the space in resolidification were occurring.

Most significantly, in this figure there is essentially no presence of polymer in the form of recognizable particles still having the form that they had when the powder was prepared prior to 3D-printing. It is believed that this complete change of morphology away from the shape of individual particles is because the leisurely nature of solvent vapor curing allows all of the polymeric material to absorb enough chloroform to become thoroughly softened and spreadable, and then the softened or liquefied polymer spreads into a film form along the surfaces of the water-soluble structure until it reaches an equilibrium or fully-spread position. When the chloroform vapor is removed, the softened and spread polymer then hardens in the morphology shown.

It is sufficient to put these typical porous samples (dimensions of the order of 1-2 centimeters maximum) in chloroform vapor for a few minutes to achieve solvent vapor fusing also called filming, or film forming. Longer exposure times (e.g., hours) are not harmful, but a few minutes of exposure is sufficient.

Example 2

This example compares the macrostructure of polymer structures which were 3D-printed using the water printing solvent vapor fusing of the present invention against the macrostructure of polymer structures which were 3D-printed using conventional dispensing of liquid chloroform onto a powder bed operating using the dissolution/resolidification mechanism. Both powder beds contained a water-soluble porogen for later leaching out as an aid to creating porosity in the finished biostructure.

Figure 10:
FIG. 10 is a digital image of two similar parts, the part on the left having been made by conventional dispensing of liquid chloroform, the part on the right having been made by a process of an invention hereof.

FIG. 10 shows a face or top view of a structure. Actually, the two images in that figure are of not exactly the same part of a complicated structure. The sample on the right, printed by a process of a present invention, illustrates a sort of a screen structure. The sample on the left, printed by conventional dispensing of liquid chloroform, illustrates a structure which is sort of a collection of posts. Nevertheless, the size scales are the same and so there is validity in comparing the fuzziness or sharpness of the two structures. It can be seen that the edge definition and sharpness are better with the printing method of a present invention (on the right).

Figure 11:
FIG. 11 is digital image of the same features printed by two different methods, showing printing with liquid chloroform on the left and printing with liquid water followed by solvent vapor filming fusing of an invention hereof, on the right.

FIG. 11 (which is the same as FIG. 1) is a side view of the same features printed by the two different methods. It shows that sharper printing and better removal of unbound powder are achieved using a method of a present invention (on the right) as compared to a conventional printing process with liquid chloroform on the left.

Example 3

Figure 12:
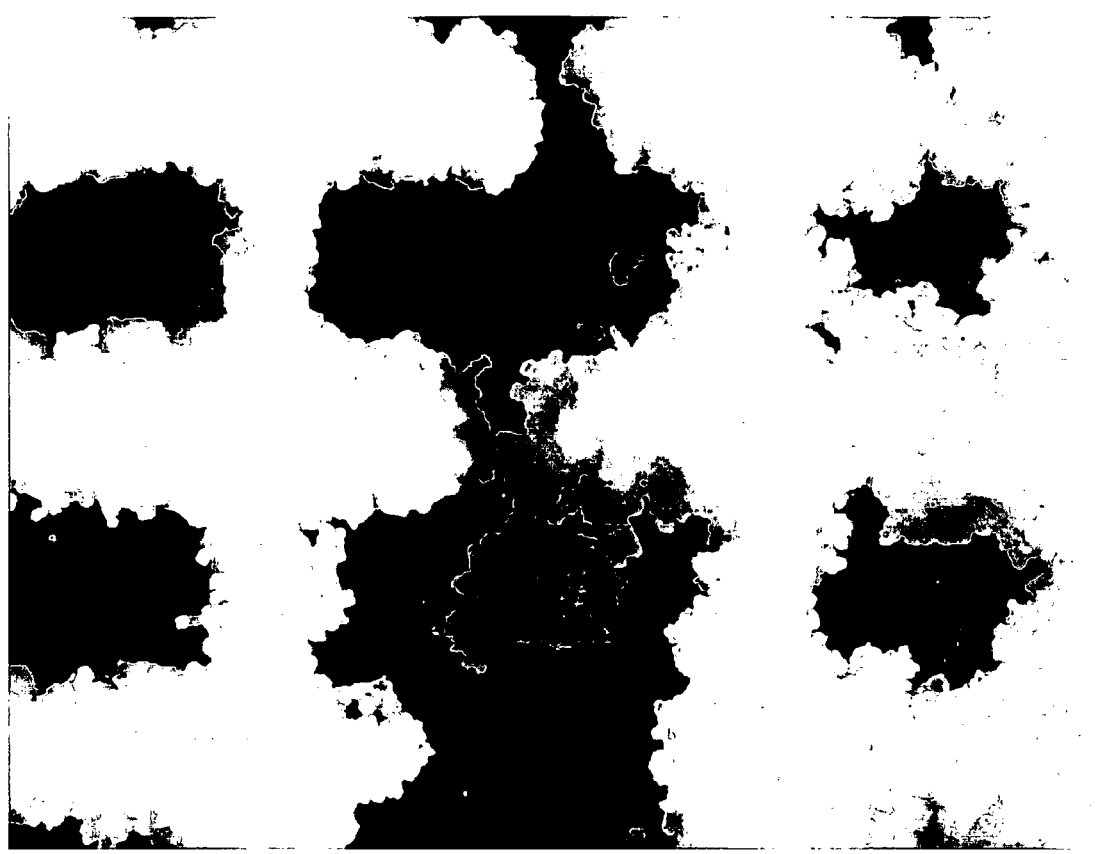
FIG. 12 is a digital image of the same features of similar parts showing printing water only on the right, and printing a sucrose solution on the left, both into powder that contains sucrose. Neither has been vapor filmed.

The next example, shown in FIG. 12, compares printing onto the same powder bed composition with a pure water binder liquid (right) and printing with a binder liquid that is a solution of sucrose in water (left). It is believed that the structure resulting from the sucrose solution printing is better held together, and the structure with pure water is more flaky. It is believed that the presence of the sucrose provides binding with less dependence on dissolution taking place during the 3DP process itself, and results in somewhat better filling of spaces between particles and attachment of particles to each other.

It is believed that the sucrose solution has different wetting characteristics from plain water. It is believed that the sucrose solution causes more powder rearrangement (powder particles pulling closer to each other during the time when they are wet), which means that the primitive features thus formed pull slightly away from the bulk powder, which results in better distinction between wet (printed) and dry (un-printed) regions, and hence less bleeding, and hence crisper and finer feature definition and also better structural characteristics.

Example 4

Figure 13C:
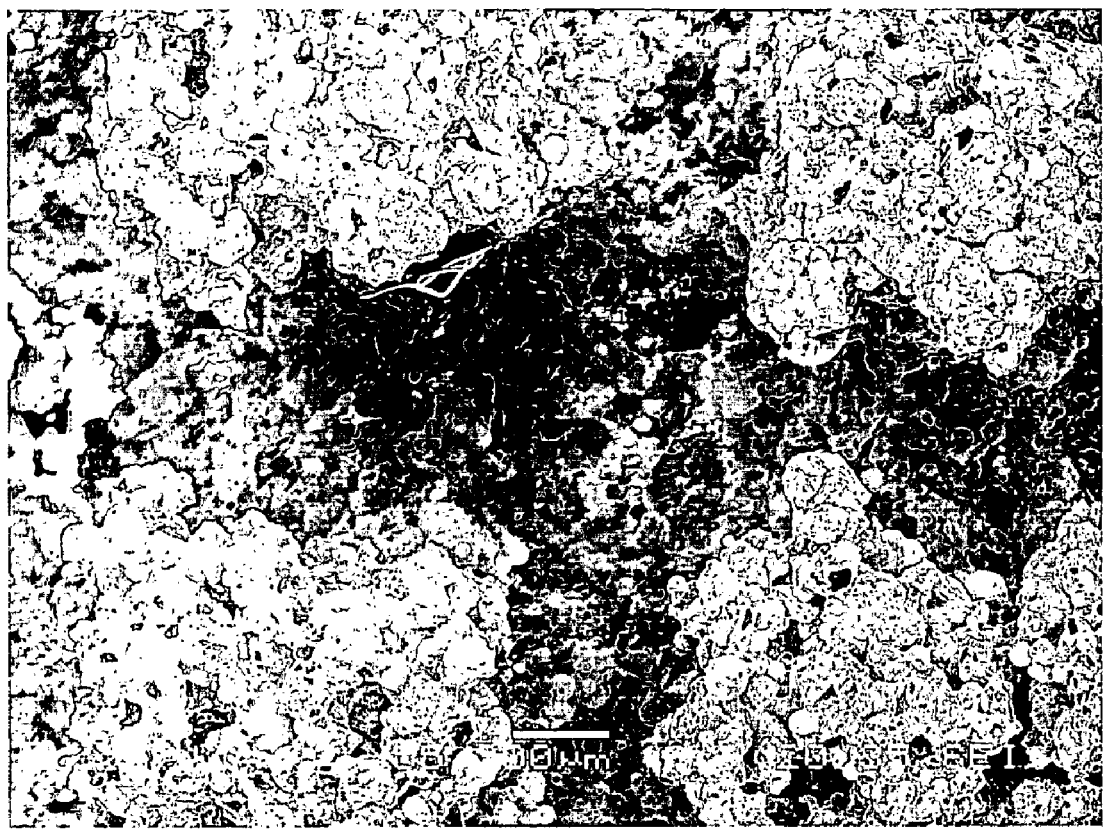
FIG. 13C is a digital image of an electromicrograph of the part shown in FIG. 13A, at a magnification of ×55.
Figure 13D:
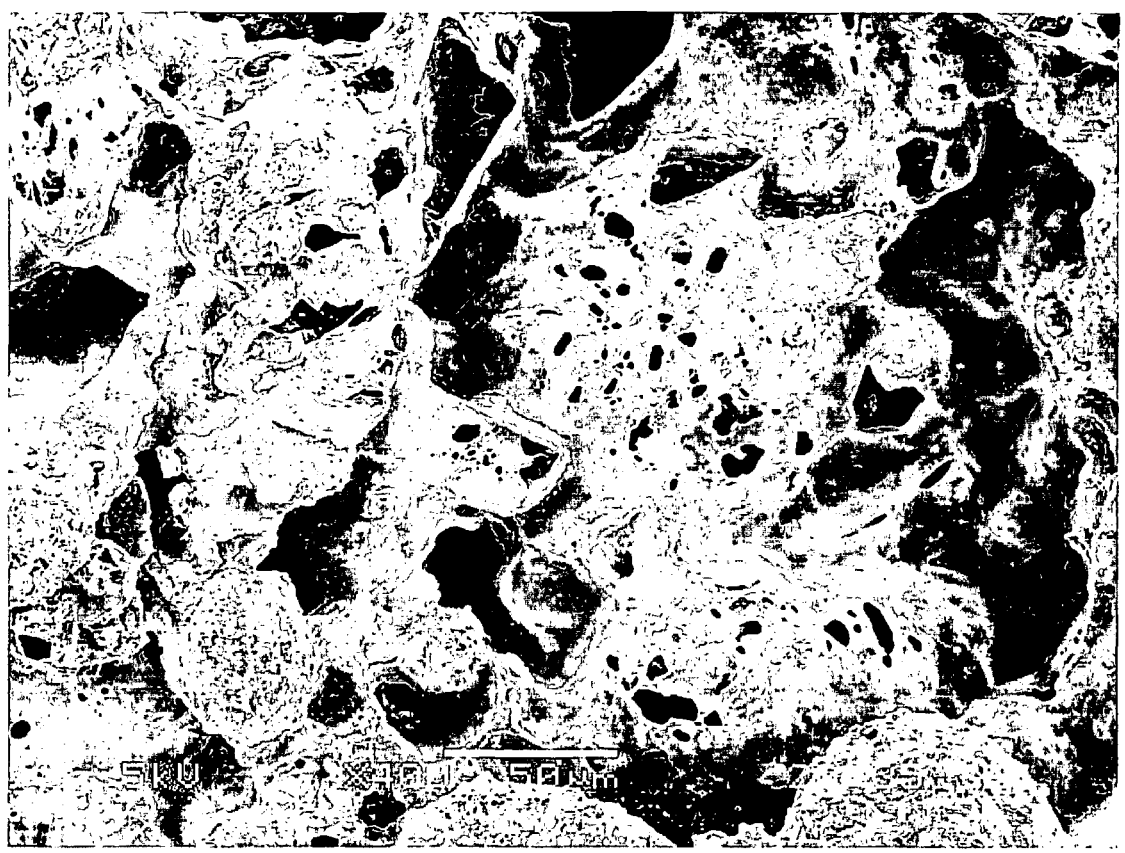
FIG. 13D is a digital image of an electromicrograph of the part shown in FIG. 13A, at a magnification of ×400.
Figure 13E:
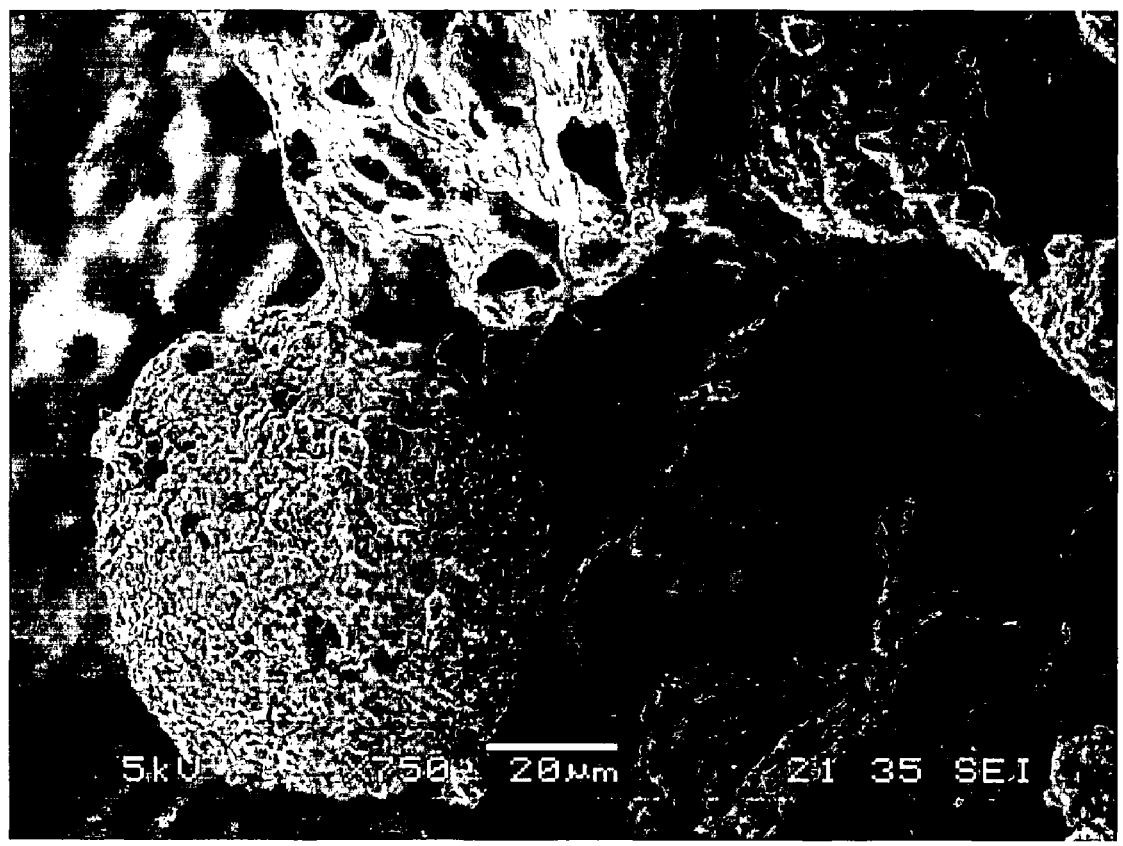
FIG. 13E is a digital image of an electromicrograph of the part shown in FIG. 13A, at a magnification of ×750.

The next example, shown in FIGS. 13A-13E demonstrated printing with an aqueous binder liquid (pure water) onto a powder bed which comprised not only polymer and water-soluble material, but also tricalcium phosphate. The composition of the powder was 20% PCL (polycaprolactone), 20% TCP, 60% Sugar. After three-dimensional printing, the preform was exposed to solvent vapor fusing. After solvent vapor fusing, the sugar was leached out with water. Articles so made, shown in FIGS. 13A and 13B at two different magnifications, have a squeezability which can readily be felt, and they also contain tricalcium phosphate for encouraging bone ingrowth, and they also contain macrochannels 1330 as illustrated in FIGS. 13A and 13B. FIGS. 13C, 13D and 13E show the same sample at greater magnifications of ×55, ×400 and ×750, respectively.

Example 5

Figure 14:
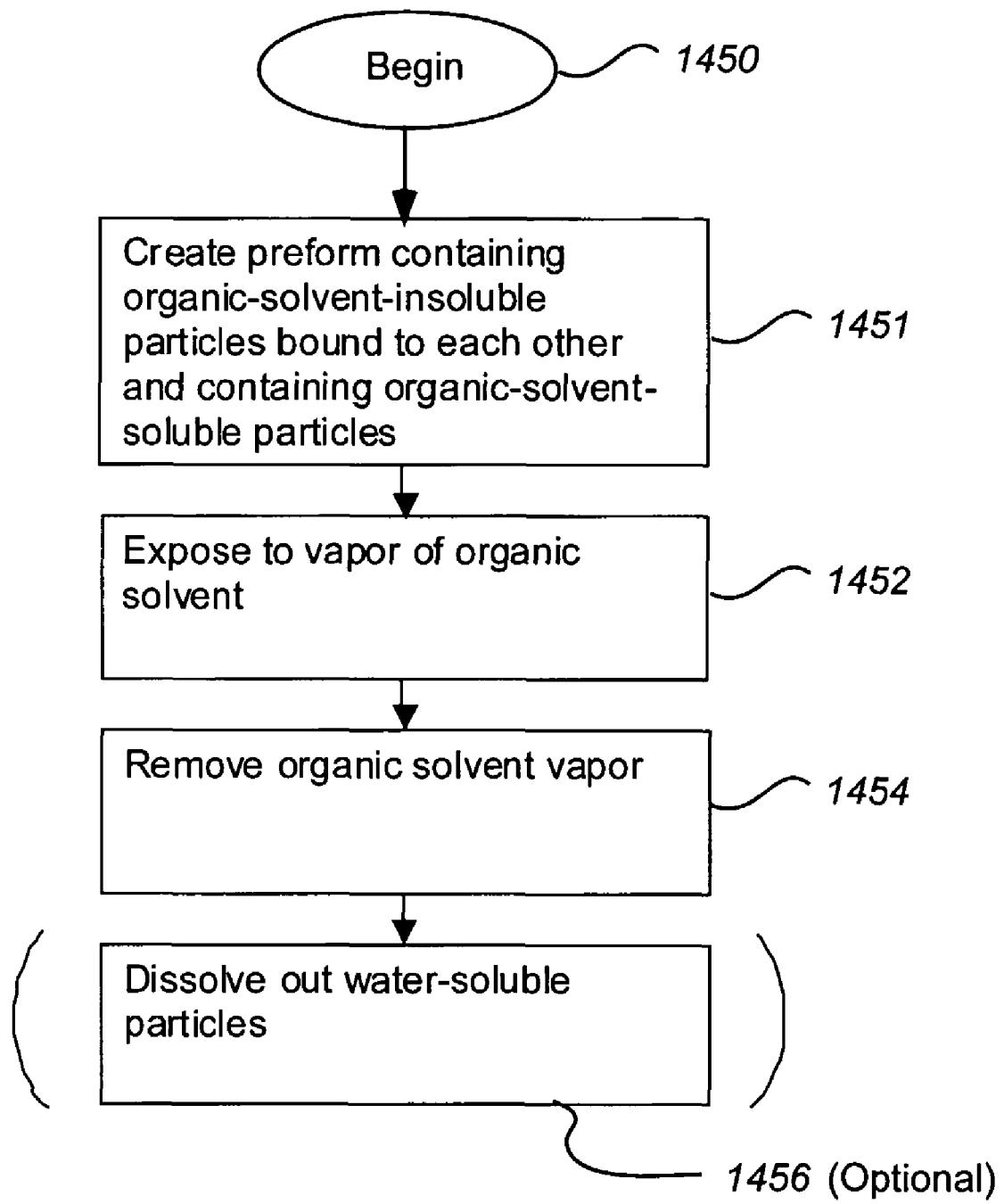
FIG. 14 is a schematic flow chart showing a method of an invention hereof using a preform that is created by a method other than three dimensional printing.

The next example, illustrated with reference to FIG. 14, illustrates that the solvent vapor fusing and porogen technique can be used with manufacturing processes other than three-dimensional printing.

For such an invention, it is necessary to make 1451 a preform which contains organic-solvent-insoluble particles bound to each other and which further contains organic-solvent-soluble particles. For example, a mixture of organic-solvent-soluble and organic-solvent-insoluble particles, possibly including a binder substance, can be formed into a desired shape by other means such as molding, casting, or other means, which can include removal of material (cutting).

The organic-solvent-insoluble particles can include water-soluble particles. As already described, water-soluble particles can include more than one substance which may be selected for their characteristics such as rate of dissolution in water, tendency to absorb water, etc. Different components may have their own particle size and particle size distribution. The organic-solvent-insoluble particles can be held together by joining each other or by an appropriate binder substance, any of which results in a preform.

The organic-solvent-insoluble particles can also include insoluble particles as described elsewhere herein.

Once the preform has a definite shape, the preform can be exposed 1452 to vapor of an organic solvent in which the organic-solvent-soluble particles are soluble. This can be done at a suitable vapor concentration and for a suitable time and for suitable values of any other relevant parameters, so as to cause at least some joining of organic-solvent-soluble particles to other organic-solvent-soluble particles. Then, the preform can be exposed 1454 to conditions free of organic solvent so that organic solvent already in the preform can leave.

Finally, if desired, the water-soluble substances can be leached out 1456.

Example 6

Figure 15:
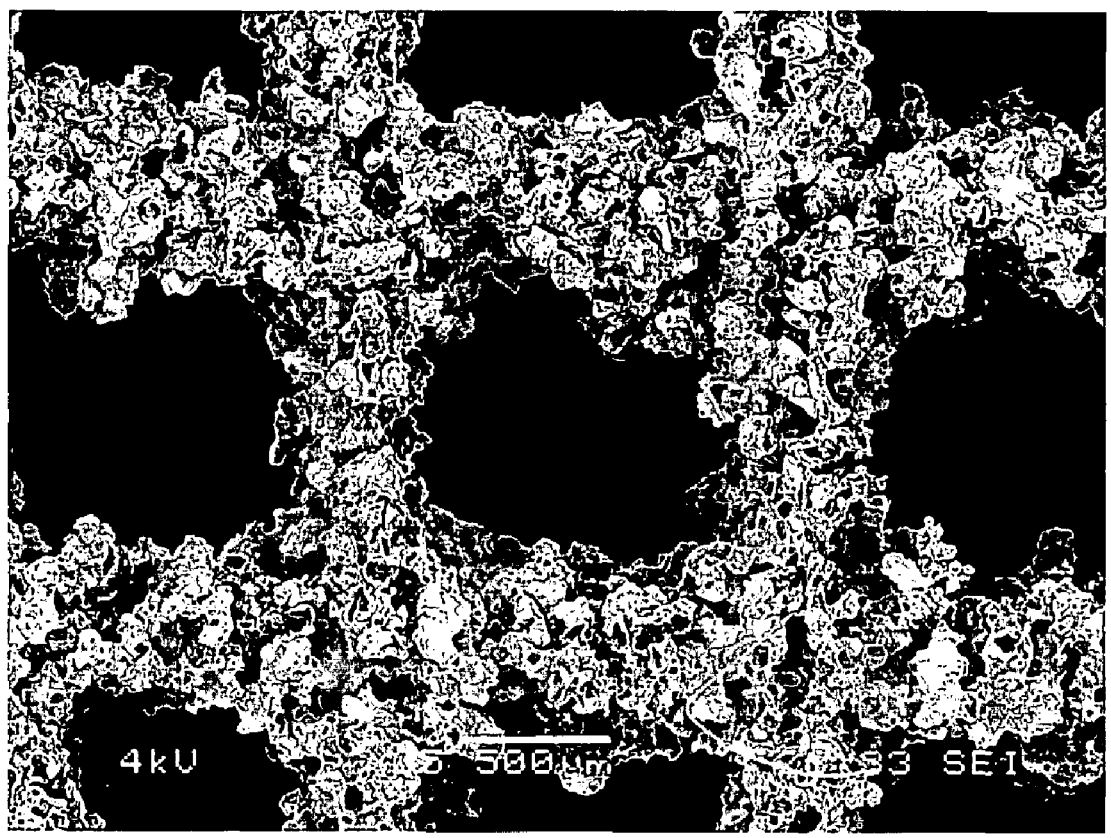
FIG. 15 is a digital image showing large scale features and small scale porosity.

FIG. 15 illustrates the large-scale features which are the overall grid shape, which is defined by the 3DP process, and small-scale porosity (which are all the smaller features), which are defined largely by the powder and related fusing and leaching steps, using water based printed binder and solvent film forming, or fusing.

The fusing of the organic-solvent-soluble particles has up until now been described as resulting from exposure to vapor of an organic solvent. While this is certainly a way of accomplishing fusing of the organic-solvent-soluble substance (polymer), it is not the only possible way.

Using Heat to Form Film

As a second method of filming material, it is possible to heat the bound preform to an appropriate temperature for an appropriate time such that the particles of a water insoluble, heat filmable material melt or soften and flow over surfaces of a structure formed by a water soluble heat resistant material to form a film. The temperature used for heat-filming may be selected to avoid causing thermal degradation of the polymers and any other substances present in the organic-solvent-soluble material. If the heat filmable material further includes bioactive substances such as one or more active pharmaceutical ingredient, a temperature for heat filming may be selected to avoid thermal damage to those substances as well. A duration for heat filming may also be selected suitable to result in a sufficient degree of filming. It is believed that at the filming temperature, the softened or liquefied heat filmable material will coalesce in a manner similar to that which has already been described for solvent vapor filming. When the preform is brought back to a lower temperature, the heat-filmed material will harden in its new configuration.

What is important for a first embodiment of such a heat filmable method of an invention hereof is that there be in the particle material: a first type of powder that is soluble by a liquid solvent, such as water, but that is resistant to softening under heated conditions; and that there be a second particle material that is solvent-insoluble, but that is filmable upon heating. Thus, the desired shape can be printed in the particle bed with the liquid solvent, which causes initial joining of particles that the solvent has contacted, but not the insoluble particles. The liquid solvent may be water, or, alcohol, or an inorganic solvent or any solvent. Loose particles are removed. Then the entire body is heated to a temperature that causes filming of the heat filmable material, as described above. Finally, the solvent is again applied, but perhaps to a greater degree, to dissolve and remove all of the solvent soluble material from the structure, leaving only the heat filmable material. Of course, if the solvent is an organic solvent, then the operator must accommodate the difficulties of using such a solvent. However, the operator does get the advantages of a method of the invention described above, where a film is formed around a temporarily formed organic-solvent-soluble structure.

It is possible that both of the above two processes (solvent vapor filming, heat filming) could be performed, in combination and/or in sequence, to cause the desired filming of material. For example, exposure to solvent vapor could be performed at a temperature warm enough so that the temperature also contributes to softening of a material that is both organic-solvent-soluble and heat flowable. Or a solvent vapor could be applied to cause initial softening and flowing, followed by elevated temperatures to cause further flowing of material. Or, the elevated temperature could be applied first, followed by solvent vapor.

Supercritical $CO_2$ is known to have solubility properties which can allow it to replace halogenated hydrocarbons and related organic solvents for cleaning purposes, and it is widely used for the extraction of caffeine from coffee and tea. Above critical temperature (31° C.) and critical pressure (72.8 atm), the vapor and liquid phases of $CO_2$ become indistinguishable, and the resulting supercritical fluid substance undergoes significant increase in solvent power, and the solvency is known to be strongly dependent on the pressure.

It is known that some polymers can be dissolved by supercritical carbon dioxide. For example, PLGA is believed to be soluble in supercritical $CO_2$. In the present invention, it is possible that the substance chosen for vapor fusing may comprise a non-halogenated substance such as supercritical carbon dioxide ($CO_2$). For the purposes of the present invention, the use of supercritical $CO_2$ would obviate the need for exposure of the biostructure to cytotoxic materials such as chloroform or methylene chloride. In addition, it may be further contemplated that even in the cases in which chloroform, methylene chloride, or similar organic solvents are used for the vapor fusing step, a subsequent treatment with supercritical $CO_2$ may be used to reduce the residual solvent level and improve safety and efficacy of the resulting biostructure.

Methods of Inventions Using Different Solvents and Conditions

The foregoing discussion has focused generally on using organic-solvent-soluble-water-insoluble materials with water-soluble-organic-solvent-insoluble materials, in one general case, and also using water-soluble materials that are not susceptible to degradation under certain heat conditions, along with materials that do soften and form films under heat conditions.

A general logic of a method invention hereof, is to provide a bound preform that is composed of at least two different types of particles: one that is soluble by a first solvent or condition, but insoluble by a second solvent or condition; and a second that is the opposite, namely insoluble by the first solvent or condition but soluble by the second solvent or condition. In fact, soluble and insoluble are more restrictive than meant here in this generalization discussion. The first particulate material must respond to the first solvent or condition by forming a bound interconnected body with sufficient strength and integrity to withstand subsequent processing, and also must be such that particles of the second material bind to the formed interconnected body. The second particulate material must be substantially unresponsive and remain intact in response to the first solvent or condition, and must respond to the second solvent or condition by forming a film that is in close contact with the surface of the interconnected body formed by the first type of particles. The first type of particles must be unresponsive and remain bound and intact in the presence of the second solvent or condition, so that the second type of particles can flow and form a film that uses the bound first particle body as a form, or template. The first type of particles must further respond to the first solvent or condition, or a third solvent or condition to which the second type of particles, after formed into a film, remains intact, so that the bound body of first particles, in response to the first condition again, or a third condition, unbinds, dissolves or melts away, leaving only the film that formed from the second type of particles.

The following summary of this aspect of an invention hereof uses the word condition to mean either a solvent (liquid or vapor) or other environmental condition, such as heat, and uses the word responsive to mean soluble, or filmable. There can be a first type of particles that is responsive to a first condition and that is substantially non-responsive to a second condition, mixed with a second type of particles that is responsive to the second condition, but not to the first. The first condition is invoked, and a bound geometry is formed in the particle collection, from bound particles of the first type, to which are also bound particles of the second type. Particles that are not bound are removed. The second condition is invoked, and a film of the second type of particles forms closely following surfaces of the bound body of first type of particles. The first condition is invoked again, possibly in a different form. For instance the first instance of the first condition could have been printed water, and the subsequent instance of the first condition could be immersion in water. Or, rather than exploiting the same phenomena, after invoking the second condition, it is possible to invoke a related or different condition to which the first type of particles are responsive. In any case, the bound body of the first type of particles is removed.

Method of Use, Applications

The articles of the present inventions can be used as substitutes for bone for repairing and healing osseous defects or for the conduction or induction of bone into a desired area such as a spinal cage. They can also be used as tissue scaffolds for growth of any sort of tissue either inside or outside the body. The springiness of the articles means that they might be able to be installed into a confined space by squeezing them and allowing them to spring back and fill space. For example, this could provide continuing contact force between the implant and the neighboring bone or other tissue, which would promote guided tissue growth. Also, a compressible scaffold could be folded or rolled or compressed and delivered to a specified site in the compressed state. Once delivered to the site, the confined scaffold could expand or unfold or configure itself to the shape of a tissue void. This would fit in well with minimally invasive surgical techniques, which emphasize minimizing the size of articles at the time they are introduced into the surgical site through openings in the skin.

The springiness could promote a good fit to a defect and could limit undesired migration or micromotion. Flexibility of the scaffold could be particularly useful for reconstruction of soft tissue such as ligaments or breast tissue or cosmetic applications.

Further Comments and Summary and Advantages

A process of a present invention enables the production of porous articles whose networks or structures include materials that are only soluble in organic solvents, and those networks or structures can contain a considerable degree of geometric complexity (which is attainable only through three-dimensional printing). Nevertheless, this process eliminates the need for dispensing of organic solvent from a printhead, which is a step fraught with some technical difficulties and, in the case of chloroform, requires printing at a saturation parameter which is not conducive to achieving fine feature sizes.

A process of a present invention also eliminates the need for the entire operating region of the 3DP machine to be exposed to vapors of organic solvents such as chloroform and eliminates the need for the printhead fluid handling system to be designed for handling organic solvents such as chloroform. In a process of a present invention, the printing parameters are determined largely by the properties of the water-soluble powders which can be printed upon with water-based binder liquids.

Another feature of this invention which can be appreciated is that it decouples the polymer fusing from the three-dimensional printing. In tissue engineering research, many polymers are being experimented with for use as scaffolds. In three dimensional printing, it is known that adjustments and optimizations often have to be made which are unique to specific polymers and solvents and printing conditions.

With solvent fusing, the fusing of the polymer into a structure occurs separately from the 3DP process. This means that the 3DP process can be somewhat standardized based largely on the properties and composition of the organic-solvent-insoluble powder components (the sugars and salts) and their binder liquid (which might be as simple as pure water). The 3DP process will not have to be adjusted each time the polymer may be changed, because the polymer is not really an active participant in the 3DP process, i.e., the polymer undergoes no significant physical or chemical change during the actual 3DP process. The undergoing of significant physical change by polymer occurs separately at a later step, and in a setting which is fairly simple. The principal variable influencing the vapor solvent fusing process is the time duration of exposure to the solvent vapor. The use of water-soluble particles which are later dissolved out helps to create pores of controlled size, and in particular is helpful for creating high porosity. In particular, the use of a mix of water-soluble particles some of which are less water-soluble than others helps to preserve the size of the less-water-soluble particles as templates for the creation of pores. Ordinarily in a dissolution/resolidification situation it would be difficult to preserve the size of particles as templates for the creation of pores.

An article of an invention hereof can be used as a bone repair implant. It contains geometric features known to be conducive to bone ingrowth. The product can be squeezed and press-fitted into a cavity similar to the way in which foam earplugs can be compressed and inserted into the ear canal. Any empty space, either at the size scale of pores or at the size scale of macroscopic polymer-free features, can contain useful biological substances, can contain useful biological substances including growth factors, cells, Active Pharmaceutical Ingredients, etc.

Many techniques and aspects of the inventions have been described herein. The person skilled in the art will understand that many of these techniques can be used with other disclosed techniques, even if they have not been specifically described in use together.

This disclosure describes and discloses more than one invention. The inventions are set forth in the claims of this and related documents, not only as filed, but also as developed during prosecution of any patent application based on this disclosure. The inventors intend to claim all of the various inventions to the limits permitted by the prior art, as it is subsequently determined to be. No feature described herein is essential to each invention disclosed herein. Thus, the inventors intend that no features described herein, but not claimed in any particular claim of any patent based on this disclosure, should be incorporated into any such claim.

Some assemblies of hardware, or groups of steps, are referred to herein as an invention. However, this is not an admission that any such assemblies or groups are necessarily patentably distinct inventions, particularly as contemplated by laws and regulations regarding the number of inventions that will be examined in one patent application, or unity of invention. It is intended to be a short way of saying an embodiment of an invention.

An abstract is submitted herewith. It is emphasized that this abstract is being provided to comply with the rule requiring an abstract that will allow examiners and other searchers to quickly ascertain the subject matter of the technical disclosure. It is submitted with the understanding that it will not be used to interpret or limit the scope or meaning of the claims, as promised by the Patent Office's rule.

The foregoing discussion should be understood as illustrative and should not be considered to be limiting in any sense. While the inventions have been particularly shown and described with references to preferred embodiments thereof, it will be understood by those skilled in the art that various changes in form and details may be made therein without departing from the spirit and scope of the inventions as defined by the claims.

The corresponding structures, materials, acts and equivalents of all means or step plus function elements in the claims below are intended to include any structure, material, or acts for performing the functions in combination with other claimed elements as specifically claimed.

What is claimed is:

1. A method of fabricating an article of manufacture, the method comprising:
   a. forming at least one particle mixture by mixing particles of an organic-solvent-soluble, water-insoluble material and particles of a water-soluble, organic-solvent-insoluble material;
   b. manufacturing an article by causing particles of the water-soluble, organic-solvent-insoluble material in the particle mixture to bind to other particles of the water-soluble, organic-solvent-insoluble material to form a water-soluble, organic-solvent-insoluble structure that also binds particles of the organic-solvent-soluble, water-insoluble material;
   c. forming a film of the organic-solvent-soluble, water-insoluble material by causing particles of the organic-solvent-soluble, water-insoluble material to soften and at least partially flow to form a film adjacent to surfaces of the water-soluble, organic-solvent-insoluble material; and
   d. providing conditions such that the organic-solvent-soluble, water-insoluble material hardens.

2. The method of claim 1, the step of forming a film comprising forming a film of the organic-solvent-soluble, water-insoluble material that substantially conforms to surfaces of the water-soluble, organic-solvent-insoluble material.

3. The method of claim 1, further wherein the step of causing particles of the water-soluble, organic-solvent-insoluble material in the particle mixture to bind to other particles of the water-soluble, organic-solvent-insoluble material comprises contacting the particle mixture with an aqueous solution of a water-soluble, organic-solvent-insoluble material.

4. The method of claim 1, further comprising, after the filming of the organic-solvent-soluble, water-insoluble material, exposing the article to water under conditions suitable to dissolve at least some of the water-soluble, organic-solvent-insoluble structure.

5. The method of claim 1, wherein the water-soluble, organic-solvent-insoluble material comprises at least one substance selected from the group consisting of salts and sugars.

6. The method of claim 1, wherein the water-soluble, organic-solvent-insoluble material comprises at least one substance selected from the group consisting of sodium chloride, sucrose, fructose and lactose.

7. The method of claim 1, wherein the water-soluble, organic-solvent-insoluble material comprises a substance having a relatively higher rate of dissolution in water and a substance having a relatively lower rate of dissolution in water.

8. The method of claim 7, further wherein the relatively higher dissolution rate substance has a rate of dissolution in water, by weight at room temperature, which is at least two times a rate of dissolution in water, by weight at room temperature, of the relatively lower dissolution rate substance.

9. The method of claim 7, wherein the relatively lower dissolution rate substance is present in the particle mixture in particle sizes that correspond to a specified pore size in the article.

10. The method of claim 7, wherein the relatively higher dissolution rate substance is present in the particle mixture in particle sizes which are generally smaller than particle sizes of the relatively lower dissolution rate substance.

11. The method of claim 1, wherein forming the particle mixture comprises mixing particles of an organic-solvent-soluble, water-insoluble material, and particles of a water-soluble, organic-solvent-insoluble material, and particles of a substantially insoluble material.

12. The method of claim 11, wherein the particles of substantially insoluble material comprise a compound that comprises calcium and a group containing phosphorus and oxygen.

13. The method of claim 1, wherein the step of fabricating the article comprises molding the particle mixture to cause particles of the water-soluble, organic-solvent-insoluble material to bind to other particles of the water-soluble, organic-solvent-insoluble material.

14. The method of claim 1, wherein manufacturing the article comprises:
   a. depositing a layer of particles comprising the particle mixture;
   b. depositing onto the layer of particles in selected places an aqueous liquid suitable to cause particles of the water-soluble, organic-solvent-insoluble material to bind to other particles of the water-soluble, organic-solvent-insoluble material;
   c. repeating the above steps a and b as many times as needed to create a shape; and
   d. removing unbound particles.

15. The method of claim 14, wherein depositing the aqueous liquid comprises depositing water.

16. The method of claim 14, wherein depositing the aqueous liquid comprises depositing a solution of a binder substance in water.

17. The method of claim 14, wherein depositing the aqueous liquid comprises depositing a solution of the water-soluble, organic-solvent-insoluble material.

18. The method of claim 14, wherein depositing the aqueous liquid comprises depositing the aqueous liquid at a saturation parameter of less than approximately 20%.

19. The method of claim 14, wherein depositing the aqueous liquid comprises depositing the aqueous liquid at a saturation parameter of less than approximately 50%.

20. The method of claim 14, wherein depositing the layers of particles comprises depositing a layer of a first particle mixture that comprises a first composition of organic-solvent-soluble, water-insoluble material and further comprises depositing a layer of a second particle mixture that comprises a second composition of organic-solvent-soluble, water-insoluble material.

21. The method of claim 14, wherein depositing the layers of particles comprises depositing a layer of a first particle mixture which comprises a substantially insoluble material and also depositing a layer of a second particle mixture which is free of any substantially insoluble material.

22. The method of claim 14, wherein depositing the layers of particles comprises depositing a layer of a first particle mixture which comprises a first composition of water-soluble, organic-solvent-insoluble material, and also depositing a layer of a second particle mixture which comprises a second composition of water-soluble, organic-solvent-insoluble material.

23. The method of claim 14, wherein depositing the layers of particles comprises depositing a layer of a first particle mixture which comprises a first average particle size, and depositing a layer of a second particle mixture which comprises a second average particle size.

24. The method of claim 1, wherein the organic-solvent-soluble, water-insoluble material comprises a polymer or copolymer.

25. The method of claim 1, wherein the organic-solvent-soluble, water-insoluble material comprises a substance selected from the group consisting of:
   polycaprolactone, members of the poly lactic co-glycolic acid family, polymethyl methacrylate, and comb polymers.

26. The method of claim 1, wherein forming the film of the organic-solvent-soluble, water-insoluble material comprises exposing the article to a vapor of an organic solvent in which the organic-solvent-soluble, water-insoluble material is soluble, under suitable conditions and for a suitable duration to cause organic-solvent-soluble, water-insoluble material in the article to soften and form a film.

27. The method of claim 26, wherein exposing the article to the vapor of an organic solvent comprises exposing the article to the vapor of a halogenated hydrocarbon.

28. The method of claim 26, wherein exposing the article to the vapor of an organic solvent comprises exposing the article to the vapor of chloroform.

29. The method of claim 1, wherein causing the organic-solvent-soluble, water-insoluble material to flow comprises exposing it to an organic solvent, and providing conditions such that the organic-solvent-soluble, water-insoluble material hardens comprises causing enough of the organic solvent to escape from the organic-solvent-soluble, water-insoluble material so that the organic-solvent-soluble, water-insoluble material hardens.

30. The method of claim 1, wherein the forming the film of the organic-solvent-soluble, water-insoluble material comprises heating the article to a suitable temperature for a suitable duration to cause organic-solvent-soluble, water-insoluble material in the article to soften and form a film.

31. A method of fabricating an article of manufacture, comprising the steps of:
   a. depositing a layer of particles comprising a particle mixture of particles of an organic-solvent-soluble, water-insoluble material and particles of a water-soluble, organic-solvent-insoluble material;
   b. depositing onto the layer of particles in selected places an aqueous liquid suitable to cause particles of the water-soluble, organic-solvent-insoluble material to bind to other particles of the water-soluble, organic-solvent-insoluble material, thereby causing particles of the water-soluble, organic-solvent-insoluble material to bind to other particles of the water-soluble, organic-solvent-insoluble material to form a water-soluble, organic-solvent-insoluble structure that also binds particles of the organic-solvent-soluble, water-insoluble material;
   c. repeating the above steps a and b to create a shape;
   d. removing unbound particles;
   e. forming a film of the organic-solvent-soluble, water-insoluble material by causing particles of the organic-solvent-soluble, water-insoluble material to soften and at least partially flow to form a film adjacent to surfaces of the water-soluble, organic-solvent-insoluble material; and
   f. providing conditions such that the film of organic-solvent-soluble, water-insoluble material hardens.

32. The method of claim 31, wherein the step of depositing aqueous liquid comprises depositing water.

33. The method of claim 31, wherein depositing the aqueous liquid comprises depositing a solution of a binder substance in water.

34. The method of claim 31, wherein depositing the aqueous liquid comprises depositing the aqueous liquid at a saturation parameter of less than approximately 20%.

35. The method of claim 31, wherein depositing the aqueous liquid comprises depositing the aqueous liquid at a saturation parameter of less than approximately 50%.

36. The method of claim 31, wherein depositing the layers of particles comprises depositing a layer of a first particle mixture that comprises a first composition of organic-solvent-soluble, water-insoluble material and further comprises depositing a layer of a second particle mixture that comprises a second composition of organic-solvent-soluble, water-insoluble material.

37. The method of claim 31, wherein depositing the layers of particles comprises depositing a layer of a first particle mixture which comprises a substantially insoluble material and also depositing a layer a second particle mixture which is free of any substantially insoluble material.

38. The method of claim 31, wherein depositing the layers of particles comprises depositing a layer of a first particle mixture which comprises a first composition of water-soluble, organic-solvent-insoluble material, and also depositing a layer of a second particle mixture which comprises a second composition of water-soluble, organic-solvent-insoluble material.

39. The method of claim 31, wherein depositing the layers of particles comprises depositing a layer of a first particle mixture which comprises a first average particle size, and depositing a layer of a second particle mixture which comprises a second average particle size.

40. A method of fabricating an article of manufacture, the method comprising:
   a. forming at least one particle mixture by mixing particles of water-insoluble material having a relatively low softening temperature and particles of a water-soluble material having a relatively higher softening temperature;
   b. manufacturing an article by causing particles of the water-soluble material in the particle mixture to adhere to other particles of the water-soluble material to form a water-soluble structure that also holds particles of the water-insoluble material;
   c. forming a film of the water-insoluble material by heating the water-soluble structure to a temperature sufficient to causing particles of the water-insoluble material to soften and at least partially flow to form a film adjacent to surfaces of the water-soluble material, at a temperature below that which would cause particles of the water-soluble material to soften and flow; and
   d. providing conditions such that the water-insoluble material hardens.

41. The method of claim 40, further comprising the step of applying water to the water-soluble structure, so that the water-soluble particles dissolve into the water, leaving a water-insoluble film adjacent to locations previously occupied by water soluble particles.

42. A method of fabricating an article of manufacture, the method comprising:
   a. forming at least one particle mixture by mixing particles of first material that is responsive to a first condition by binding with adjacent particles of the first material and not responsive to a second condition, and particles of a second material that is responsive to the second condition by filming with adjacent particles of the second material and not responsive to the first condition;
   b. manufacturing an article by establishing the first condition, thereby causing particles of the first material in the particle mixture to bind to other particles of the first material to form a structure that is responsive to the first condition and that also binds particles of the second material;
   c. establishing the second condition, thereby forming a film of the second material by causing particles of the second material to soften and at least partially flow to form a film adjacent to surfaces of the particles of the first material, while particles of the first material remain bound to each other; and
   d. providing conditions such that the film formed from particles of the second material hardens.

43. The method of claim 42, further comprising the step of establishing again the first condition to the bound structure of particles of the first material, so that the first material particles separate from each other and from the film formed from the particles of the second material, leaving a film adjacent to locations previously occupied by particles of the first material.

44. The method of claim 42, further comprising the step of establishing a third condition to the bound structure of particles of the first material, the particles of the first material being responsive to the third condition and the particles of the second material not being responsive to the third condition, so that the first material particles separate from each other and from the film formed from the particles of the second material, leaving a film adjacent to locations previously occupied by particles of the first material.

45. The method of claim 42, the particles of the first material comprising organic-solvent-soluble, water-insoluble material and the particles of the second material comprising water-soluble, organic-solvent-insoluble material.

46. The method of claim 42, the particles of the first material comprising first-solvent-soluble-second-solvent-insoluble material and the particles of the second material comprising second-solvent-soluble-first-solvent-insoluble material.

47. The method of claim 46, the step of establishing the first condition comprising contacting the first solvent in liquid form with the particle mixture, and the step of establishing the second condition comprising contacting the second solvent in vapor form with the particle mixture including the adhered particles of the first material.

48. The method of claim 42, the particles of the first material comprising water-soluble, high-melting-temperature material and the particles of the second material comprising low-melting-temperature, water-insoluble material.

49. The method of claim 18, the step of establishing the first condition comprising contacting water with the particle mixture, and the step of establishing the second condition comprising heating the particle mixture including the bound particles of the first material to a temperature at which the particles of the second material form a film bound to the particles of the first material.

* * * * *